(12) United States Patent
Poradosu et al.

(10) Patent No.: US 8,383,607 B2
(45) Date of Patent: Feb. 26, 2013

(54) PERIFOSINE AND CAPECITABINE AS A COMBINED TREATMENT FOR CANCER

(75) Inventors: Enrique Poradosu, Brookline, MA (US); Peeter Sportelli, North Andover, MA (US)

(73) Assignee: AEterna Zentaris GmbH, Frankfurt (DE)

( * ) Notice: Subject to any disclaimer, the term of this patent is extended or adjusted under 35 U.S.C. 154(b) by 0 days.

(21) Appl. No.: 13/077,766

(22) Filed: Mar. 31, 2011

(65) Prior Publication Data

US 2011/0243933 A1    Oct. 6, 2011

Related U.S. Application Data

(60) Provisional application No. 61/319,315, filed on Mar. 31, 2011.

(51) Int. Cl.
*A61K 31/675* (2006.01)
(52) U.S. Cl. .................................................... 514/89
(58) Field of Classification Search .................. 514/89
See application file for complete search history.

(56) References Cited

U.S. PATENT DOCUMENTS

| | | | |
|---|---|---|---|
| 5,219,866 A | 6/1993 | Schumacher et al. |
| 5,942,639 A | 8/1999 | Engel et al. |
| 6,093,704 A | 7/2000 | Nickel et al. |
| 6,172,050 B1 | 1/2001 | Nossner et al. |
| 6,538,029 B1 | 3/2003 | Thompson et al. |
| 6,583,127 B1 | 6/2003 | Gajate et al. |
| 6,696,428 B2 | 2/2004 | Nickel et al. |
| 6,800,639 B2 | 10/2004 | Giles et al. |
| 6,903,080 B2 | 6/2005 | Nossner et al. |
| 2004/0097470 A1 | 5/2004 | Engel et al. |
| 2004/0147541 A1 | 7/2004 | Lane et al. |
| 2005/0234017 A1 | 10/2005 | Zeldis |
| 2010/0189784 A1 | 7/2010 | Engel et al. |
| 2010/0190738 A1 | 7/2010 | Engel et al. |
| 2011/0028421 A1 | 2/2011 | Engel et al. |

FOREIGN PATENT DOCUMENTS

| | | |
|---|---|---|
| EP | 1 545 553 B1 | 6/2005 |
| WO | WO 99/37289 | 7/1999 |
| WO | WO 00/33917 | 6/2000 |
| WO | WO 02/066019 A2 | 8/2002 |
| WO | WO 03/055522 A1 | 7/2003 |
| WO | WO 2005/000318 | 1/2005 |
| WO | WO2006/081452 | 8/2006 |
| WO | WO2006/097323 | 9/2006 |
| WO | WO2007/011721 | 1/2007 |
| WO | WO2008/034039 | 3/2008 |
| WO | WO2009/076170 | 6/2009 |
| WO | WO 2011/123691 | 10/2011 |

OTHER PUBLICATIONS

Vukelja et al. Randomized phase II study of perifosine in combination with capecitabine versus capecitabine alone in patients with second or third line metastatic colon cancer. J. Clin. Oncol., 27: 15s, 2009 (suppl; abstr 4081).*

Richardson et al., "Perifosine Plus Bortezomib and Dexamethasone in Patients with Relapsed/Refractory Multiple Myeloma Previously Treated with Bortezomib: Results of a Multicenter Phase I/II Trial," *J. Clin. Oncol.* (2011), http://jco.ascopubs.org/cgi/doi/10.1200/JCO.2010.33.9788, 11 pages.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Oct. 17, 2011 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Oct. 16, 2011 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Jul. 26, 2011 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Jul. 19, 2011 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated May 20, 2011 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Apr. 18, 2011 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Mar. 7, 2011 (ongoing), sponsored by Keryx / AOI Pharmaceuticals, Inc.

(Continued)

*Primary Examiner* — Rei-tsang Shiao
(74) *Attorney, Agent, or Firm* — Goodwin Procter LLP

(57) ABSTRACT

Treatment regimens comprising co-treatment of cancer with perifosine and capecitabine are disclosed herein, as well as pharmaceutical compositions and unit dosage forms thereof formulated to be suitable for use in said treatment regimens.

25 Claims, 6 Drawing Sheets

OTHER PUBLICATIONS

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Feb. 17, 2011 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Jan. 11, 2011 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Dec. 15, 2010 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Nov. 22, 2010 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Nov. 4, 2010 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Oct. 9, 2010 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Sep. 28, 2010 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Aug. 27, 2010 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Aug. 4, 2010 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Jul. 16, 2010 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Jun. 28, 2010 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Jun. 2, 2010 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated May 19, 2010 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Apr. 27, 2010 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Apr. 12, 2010 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Apr. 7, 2010 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Apr. 2, 2010 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Apr. 1, 2010 (ongoing), sponsored by Keryx / AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Mar. 31, 2010 (ongoing), sponsored by Keryx / AOI Pharmaceuticals, Inc.

"A Randomized Placebo-Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Nov. 10, 2011, sponsored by Keryx / AOI Pharmaceuticals, Inc.

"A Randomized Placebo-Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Oct. 17, 2011, sponsored by Keryx / AOI Pharmaceuticals, Inc.

"A Randomized Placebo-Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated May 9, 2011, sponsored by Keryx / AOI Pharmaceuticals, Inc.

"A Randomized Placebo-Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Sep. 22, 2009, sponsored by Keryx / AOI Pharmaceuticals, Inc.

"A Randomized Placebo-Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Feb. 16, 2009, sponsored by Keryx / AOI Pharmaceuticals, Inc.

"A Randomized Placebo-Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Apr. 7, 2008, sponsored by Keryx / AOI Pharmaceuticals, Inc.
"A Randomized Placebo-Controlled Study of Perifosine in Combination With Single Agent Chemotherapy for Metastatic Cancer Patients" ( Phase II Study) recorded in ClinicalTrials.gov registry, ClinicalTrials Identifier: NCT00398879, data updated Oct. 16, 2007, sponsored by Keryx / AOI Pharmaceuticals, Inc.
"A Randomized Placebo-Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Mar. 15, 2007, sponsored by Keryx / AOI Pharmaceuticals, Inc.
"A Randomized Placebo-Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Feb. 1, 2007, sponsored by Keryx / AOI Pharmaceuticals, Inc.
"A Randomized Placebo-Controlled Study of Perifosine in Combination With Single Agent Chemotherapy for Metastatic Cancer Patients" ( Phase II Study) recorded in ClinicalTrials.gov registry, ClinicalTrials Identifier: NCT00398879, data updated Jan. 31, 2007, sponsored by Keryx / AOI Pharmaceuticals, Inc.
"A Randomized Placebo-Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Nov. 13, 2006, sponsored by Keryx / AOI Pharmaceuticals, Inc.
"A Phase I Study of Perifosine + Capecitabine for Patients With Advanced Colon Cancer" recorded in ClinicalTrials.gov registry, ClinicalTrials Identifier: NCT01048580, dated Nov. 14, 2011.
"A Phase I Study of Perifosine + Capecitabine for Patients With Advanced Colon Cancer" recorded in ClinicalTrials.gov registry, ClinicalTrials Identifier: NCT01048580, dated Oct. 17, 2011.
"A Phase I Study of Perifosine + Capecitabine for Patients With Advanced Colon Cancer" recorded in ClinicalTrials.gov registry, ClinicalTrials Identifier: NCT01048580, dated Jul. 19, 2011.
"A Phase I Study of Perifosine + Capecitabine for Patients With Advanced Colon Cancer" recorded in ClinicalTrials.gov registry, ClinicalTrials Identifier: NCT01048580, dated Mar. 31, 2010.
"A Phase I Study of Perifosine + Capecitabine for Patients With Advanced Colon Cancer" recorded in ClinicalTrials.gov registry, ClinicalTrials Identifier: NCT01048580, dated Jan. 13, 2010.
"A Phase I Study of Perifosine + Capecitabine for Patients With Advanced Colon Cancer" recorded in ClinicalTrials.gov registry, ClinicalTrials Identifier: NCT01048580, dated Jan. 12, 2010.
Argiris et al., A phase II trial of perifosine, an oral alkylphospholipid, in recurrent or metastatic head and neck cancer. Cancer Biol Ther. Jul. 2006;5(7):766-70.
ASCO Abstract 2006—Journal of Clinical Oncology, 2006 ASCO Annual Meeting Proceedings (Post-Meeting Edition)m vol. 24, No. 18S (Jun. 20 Supplement), 2006.
ASCO Abstract 2009—Journal of Clinical Oncology, 2009 ASCO Annual Meeting Proceedings (Post-Meeting Edition)m vol. 27, No. 15S (May 20 Supplement), 2009:4081.
Awada et al., An EORTC-IDBBC phase I study of gemcitabine and continuous infusion 5-fluorouracil in patients with metastatic breast cancer resistant to anthracyclines or pre-treated with both anthracyclines and taxanes. Eur J Cancer. Apr. 2002:38(6):773-8.
Ayala et al., Bortezomib-mediated inhibition of steroid receptor coactivator-3 degradation leads to activated Akt. Clin Cancer Res. Nov. 15, 2008;14(22);7511-8.
Banker and Rhodes (Eds.), *Modern Pharmaceutics*,3$^{rd}$ Edition, Revised and Expanded. pp. 451 & 596, Marcel Dekker Inc., (1996).
Bendell et al., "Randomized placebo-controlled phase II trial of perifosine plus capecitabine as second- or third-line therapy in patients with metastatic colorectal cancer". J Clin Oncol. Nov. 20, 2011;29(33 ):4394-400 Epub Oct. 3, 2011 (Epub copy only).
Berkovic et al., The influence of 1-beta-D-arabinofuranosylcytosine on the metabolism of phosphatidylcholine in human leukemic HL 60 and Raji cells. Leukemia. Dec. 1997:11(12):2079-86.
Budman and Calabro, In vitro search for synergy and antagonism: evaluation of docetaxel combinations in breast cancer cell lines. Breast Cancer Res Treat. Jul. 2002;74(1):41-6.

Cabrera-Serra et al., In vitro activity of perifosine: a novel alkylphospholipid against the promastigote Stage of Leishmania species. Parasitol Res. 2006 (Epub copy only).
Caccin et al., Neurotoxicity of inverted-cone shaped lipids. Neurotoxicology. Mar. 2009;30(2):174-81.
Carón et al., Activated forms of H-RAS and K-RAS differentially regulate membrane association of P13K, PDK-1, and AKT and the effect of therapeutic kinase inhibitors on cell survival. Mol Cancer Ther. Feb. 2005:4(2):257-70.
Castanys-Muñoz et al., A novel ATP-binding cassette transporter from Leishmania is involved in transport of phosphatidylcholine analogues and resistance to alkyl-phospholipids. Mol Microbiol. Jun. 2007;64(5):1141-53.
Catley et al., Alkyl phospholipid perifosine induces myeloid hyperplasia in a murine myeloma model. Exp Hematol. Jul. 2007;35(7):1038-46.
Chiarini et al., The novel Akt inhibitor, perifosine, induces caspase-dependent apoptosis and downregulates P-glycoprotein expression in multidrug-resistant human T-acute leukemia cells hy a JNK-dependent mechanism. Leukemia. Jun. 2008:22(6):1106-16.
Chou and Talalay, Quantitative analysis of dose-effect relationships: the combined effects of multiple drugs or enzyme inhibitors. Adv Enzyme Regul. 1984;22:27-55.
Chou TC. Drug combination studies and their synergy quantification using the Chou-Talalay method. Cancer Res. Jan. 15, 2010;70(2):440-6.
Cirstea et al., Dual inhibition of akt/mammalian target of rapamycin pathway by nanoparticle albumin-bound-rapamycin and perifosine induces antitumor activity in multiple myeloma. Mol Cancer Ther. Apr. 2010;9(4):963-75.
Coppola et al., Noninvasive imaging of apoptosis and its application in cancer therapeutics. Clin Cancer Res. Apr. 15, 2008;14(8):2492-501.
Crul et al., Phase I and pharmacological study of daily oral administration of perifosine (D-21266) in patients with advanced solid tumours. Eur J Cancer. Aug. 2002;38(12):1615-21.
Dasmahapatra et al., In vitro combination treatment with perifosine and UCN-01 demonstrates synergism against prostate (PC-3) and lung (A549) epithelial adenocarcinoma cell lines. Clin Cancer Res. Aug. 1, 2004;10(15):5242-52.
David et al., Perifosine synergistically enhances TRAIL-induced myeloma cell apoptosis via up-regulation of death receptors. Clin Cancer Res. Aug. 15, 2008;14(16):5090-8.
De Siervi et al., Transcriptional activation of p21(waf1/cip1) by alkylphospholipids: role of the mitogen-activated protein kinase pathway in the transactivation of the human p21(waf1/cip1) promoter by Sp1. Cancer Res. Jan. 15, 2004:64(2):743-50.
Dogan et al., Ocular side effects associated with imatinib mesylate and perifosine for gastrointestinal stromal tumor. Hematol Oncol Clin North Am. Feb. 2009;23(1):109-14, ix. Review.
Ellis and Crowder, "PIKing" the winner for phosphatidylinositol 3-kinase inhibitors in ErbB2-positive breast cancer: let's not "PTENed" it's easy! Clin Cancer Res. Oct. 1, 2007;13(19):5661-2.
Engel et al., Induction of programmed cell death by inhibition of AKT with the alkylphosphochloine perifosine in in vitro models of platinum sensitive and resistant ovarian cancers. Arch. Gynecol. Obstet. 2011, 283:603-610, published online Apr. 20, 2010.
Engel et al., Perifosine inhibits growth of human experimental endometrial cancers by blockade of AKT phosphrylation. Eur J Obstet Gynecol Reprod Biol. Nov. 2008:141(1):64-9.
Ernst et al., Phase II study of perifosine in previously untreated patients with metastatic melanoma. Invest New Drugs. Dec. 2005;23(6):569-75.
Festuccia et al., Akt down-modulation induces apoptosis of human prostate cancer cells and synergizes with EGFR tyrosine kinase inhibitors. Prostate. Jun. 15, 2008;68(9):965-74.
Floryk and Thompson, Perifosine induces differentiation and cell death in prostate cancer cells. Cancer Lett. Aug. 8, 2008;266(2):216-26.
Fomchenko and Holland, Mouse models of brain tumors and their applications in preclinical trials. Clin Cancer Res. Sep. 15, 2006;12(18):5288-97.

Fu et al., Perifosine inhibits mammalian target of rapamycin signaling through facilitating degradation of major components in the mTOR axis and induces autophagy. Cancer Res. Dec. 1, 2009;69(23):8967-76.

Gajate and Mollinedo, Edelfosine and perifosine induce selective apoptosis in multiple myeloma by recruitment of death receptors and downstream signaling molecules into lipid rafts. Blood. Jan. 15, 2007;109(2):711-9.

Georgieva et al., Combination effects of alkylphosphocholines and gemcitabine in malignant and normal hematopoietic cells. Cancer Lett. Aug. 28, 2002;182(2);163-74.

Ghobrial et al., Emerging drugs in multiple myeloma. Expert Opin Emerg Drugs. Mar. 2007;12(1):155-63 (Author Proof copy).

Gills and Dennis, Perifosine: update on a novel Akt inhibitor. Curr Oncol Rep. Mar. 2009;11(2):102-10. Review.

Goodman & Gillman, *The Pharmacological Basis of Therapeutic*, 9$^{th}$ Edition, pp. 1225-1232 (1996).

Granville et al., Handicapping the race to develop inhibitors of the phosphoinositide 3-kinase/Akt/mammalian target of rapamycin pathway. Clin Cancer Res. Feb. 1, 2006;12(3 Pt 1):679-89.

Grosman N. Similar effects of ether phospholipids. PAF and lyso-PAF on the Ca(2+)-ATPase activity of rat brain synaptosomes and leukocyte membranes. Int Immunopharmacol. Jul. 2001;1(7):1321-9.

Harvey and Lonial, P13 kinase/AKT pathway as a therapeutic target in multiple myeloma. Future Oncol. Dec. 2007;3(6):639-47. Review.

Hennessy Et al., Pharmacodynamic markers of perifosine efficacy. Clin Cancer Res. Dec. 15, 2007;13(24):7421-31.

Hideshima et al., Inhibition of Akt induces significant downregulation of survivin and cytotoxicity in human multiple myeloma cells. Br J Haematol. Sep. 2007;138(6):783-91.

Hideshima et al., Perifosine, an oral bioactive novel alkylphospholipid, inhibits Akt and induces in vitro and in vivocytotoxicity in human multiple myeloma cells. Blood. May 15, 2006;107(10):4053-62.

Hilgard et al., Alkylphosphocholines: a new class of membrane-active anticancer agents. Cancer Chemother Pharrnacol. 1993;32(2):90-5.

Hilgard et al., D-21266, a new heterocyclic alkylphospholipid with antitumour activity. Eur J Cancer. Mar. 1997;33(3):442-6.

Hilgard et al., "Heterocyclic alkylphospholipids with an improved therapeutics range". Chp. 26 in *Platelet-Activating Factor and Related Lipid Mediators 2*. pp. 157-164, Edited by Nigam et al., Plenum Press, New York, 1996.

Huston et al., Targeting Akt and heat shock protein 90 produces synergistic multiple myeloma cell cytotoxicity in the bone marrow microenvironment. Clin Cancer Res. Feb. 1, 2008;14(3):865-74.

International Search Report for PCT application No. PCT/US2006/002988 (or PCT publication No. WO 2006/081452) dated Nov. 22, 2007.

International Search Report for PCT application No. PCT/US2011/030800 (or PCT publication No. WO 2011/123691) dated Jul. 25, 2011.

Jendrossek and Handrick, Membrane targeted anticancer drugs: potent inducers of apoptosis and putative radiosensitisers. Curr Med Chem Anticancer Agents. Sep. 2003;3(5):343-53.

Kasianenko et al., Topical use of Miltex in patients with breast cancer's cutaneous manifestations. 1998:87 (2 pages) Poster Abstract.

Keenan et al. Perifosine-related rapidly progressive corneal ring infiltrate. Cornea. May 2010;29(5):583-5 (Epub copy only).

Knebel et al., Quantification of perifosine, an alkylphosphocholine anti-tumour agent, in plasma by pneumatically assisted electrospray tandem mass spectrometry coupled with high-performance liquid chromatography. J Chromatogr B Biomed Sci Appl. Jan. 22, 1999;721(2):257-69.

Knowling et al., A phase II study of perifosine (D-21226) in patients with previously untreated metastatic or locally advanced soft tissue sarcoma: A National Cancer Institute of Canada Clinical Trials Group trial. Invest New Drugs. Sep. 2006;24(5):435-9.

Kodach et al., Violacein synergistically increases 5-fluorouracil cytotoxicity, induces apoptosis and inhibits Akt-mediated signal transduction in human colorectal cancer cells. Carcinogenesis. Mar. 2006;27(3):508-16.

Kondapaka et al., Perifosine, a novel alkylphospholipid, inhibits protein kinase B activation. Mol Cancer Ther. Nov. 2003;2(11):1093-103.

Konecny et al., Drug interactions and cytotoxic effects of paclitaxel in combination with carboplatin, epirubicin, gemcitabine or vinorelbine in breast cancer cell lines and tumor samples. Breast Cancer Res Treat. Jun. 2001;67(3):223-33.

Konstantinov and Berger, Human urinary bladder carcinoma cell lines respond to treatment with akylphosphocholines. Cancer Lett. Oct. 1, 1999;144(2):153-60.

Konstantinov et al., Alkylphosphocholines: Effects on human leukemic cell lines and normal bone marrow cells. Int J Cancer. Aug. 31, 1998;77(5):778-86.

Konstantinov et al., BCR-ABL influences the antileukaemic efficacy of alkylphosphocholines. Br J Haematol. Nov. 1999;107(2):365-80.

Korkaya H, Paulson A, Charafe-Jauffret E, Ginestier C, Brown M, Dutcher J, Clouthier SG, Wicha MS. Regulation of mammary stem/progenitor cells by PTEN/Akt/beta-catenin signaling. PLoS Biol. Jun. 2, 2009;7(6):e1000121. Epub Jun. 2, 2009. (Epub copy only).

Kumar et al., The alkylphospholipid perifosine induces apoptosis and p21-mediated cell cycle arrest in medulloblastoma. Mol Cancer Res. Nov. 2009;7(11):1813-21.

Leighl et al., A Phase 2 study of perifosine in advanced or metastatic breast cancer. Breast Cancer Res Treat. Mar. 2008;108(1):87-92.

Leleu et al., Targeting NF-kappaB in Waldenstrom macroglobulinemia. Blood. May 15, 2008;111(10):5068-77.

Leleu et al., Waldenstrom macroglobulinemia. Cancer Lett. Oct. 18, 2008;270(1):95-107. Epub Jun. 13, 2008.

Leleu et al., The Akt pathway regulates survival and homing in Waldenstrom macroglobulinemia. Blood. Dec. 15, 2007;110(13):4417-26. Epub Aug. 30, 2007.

Li et al. Enhancement of antitumor activity of the anti-EGF receptor monoclonal antibody cetuximab/C225 by perifosine in PTEN-deficient cancer cells. Oncogene. Jan. 26, 2006;25(4):525-35.

Liu et al., Genetic alterations in the phosphoinositide 3-kinase/Akt signaling pathway confer sensitivity of thyroid cancer cells to therapeutic targeting of Akt and mammalian target of rapamycin. Cancer Res. Sep. 15, 2009;69(18):7311-9. Epub Aug. 25, 2009. Erratum in: Cancer Res. Oct. 15, 2009;69(20):8216 (Epub copy only).

Lohmeyer et al., Antitumor ether lipids and alkylphosphocholines. Drugs of the Future, 1994, 19(11):1021-1037.

Lopez et al., The synergistic and antagonistic effects of cytotoxic and biological agents on the in vitro antitumour effects of suramin. Eur J Cancer. 1994;30A(10):1545-9.

Lopiccolo et al., Targeting the P13K/Akt/mTOR pathway: effective combinations and clinical considerations. Drug Resist Updat, Feb.-Apr. 2008;11(1-2):32-50 (NIH-Public Access Author Manuscript).

Maly et al., Interference of new alkylphospholipid analogues with mitogenic signal transduction. Anticancer Drug Des. Jul. 1995;10(5):411-25.

Mitsiades et al., Emerging treatments for multiple myeloma: beyond immunomodulatory drugs and bortezomib. Semin Hematol. Apr. 2009;46(2):166-75. Review.

Miyazaki et al., Activation of caspase 3-like protease is essential to Octadecyl-(1,1-dimethyl-4-piperinino-4-YL)-phosphate(D-21266)-induced apoptosis in human squamous cell carcinoma KB cells. Drugs of Today. 1998, 34(Suppl. F):51-57.

Momota et al., Perifosine inhibits multiple signaling pathways in glial progenitors and cooperates with temozolomide to arrest cell proliferation in gliomas in vivo. Cancer Res. Aug. 15, 2005;65(16):7429-35.

Muñoz-Martínez et al., The anti-tumor alkylphospholipid perifosine is internalized by an ATP-dependent translocase activity across the plasma membrane of human KB carcinoma cells. Biochim Biophys Acta. Feb. 2008;1778(2):530-40. Epub Oct. 25, 2007.

Nelson et al., Inhibition of Akt Pathways in the Treatment of Prostate Cancer. Prostate Cancer and Prostatic Disease. (2007), 10:331-339 Epub May 1, 2007.

Nyåkern et al., Synergistic induction of apoptosis in human leukemia T cells by the Akt inhibitor perifosine and etoposide through activation of intrinsic and Fas-mediated extrinsic cell death pathways. Mol Cancer Ther. Jun. 2006;5(6):1559-70.

Osborne et al., Antagonism of chemotherapy-induced cytotoxicity for human breast cancer cells by antiestrogens. J Clin Oncol. Jun. 1989;7(6):710-7.

Page et al., A new fluorometric assay for cytotoxicity measurements in-vitro. Int J Oncol. Sep. 1993;3(3):473-6.

Papa et al., Proapoptotic activity and chemosensitizing effect of the novel Akt inhibitor perifosine in acute myelogenous leukemia cells. Leukemia. Jan. 2008;22(1):147-60.

Patel et al., Perifosine, a novel alkylphospholipid, induces p21(WAF1) expression in squamous carcinoma cells through a p53-independent pathway, leading to loss in cyclin-dependent kinase activity and cell cycle arrest. Cancer Res. Mar. 1, 2002;62(5):1401-9.

Porta and Figlin, Phosphatidylinositol-3-kinase/Akt signaling pathway and kidney cancer, and the therapeutic potential of phosphatidylinositol-3-kinase/Akt inhibitors. J Urol. Dec. 2009;182(6):2569-77.

Posadas et al., A phase II study of perifosin in androgen independent prostate cancer. Cancer Biol Ther. Oct. 2005;4(10):1133-7.

Press release dated Apr. 8, 2010, New York by Keryx Biopharmaceuticals, Inc.

Press release dated Feb. 3, 2010, New York by Keryx Biopharmaceuticals, Inc.

Press release dated Jan. 21, 2010, New York by Keryx Biopharmaceuticals, Inc.

Press release dated Jan. 25, 2010, New York by Keryx Biopharmaceuticals, Inc.

Press release dated Jun. 1, 2010, New York by Keryx Biopharmaceuticals, Inc.

Press release dated May 31, 2009, New York by Keryx Biopharmaceuticals, Inc.

Principe et al., Evaluation of combinations of antineoplastic ether phospholipids and chemotherapeutic drugs. Anticancer Drugs. Dec. 1992;3(6):577-87.

Principe et al., Synergistic cytotoxic effect of aza-alkylphospholipids in association with chemotherapeutic drugs. J. Lipid Mediators Cell Signaling 1994, (10)171-173.

Rahmani et al., Coadministration of histone deacetylase inhibitors and perifosine synergistically induces apoptosis in human leukemia cells through Akt and ERK1/2 inactivation and the generation of ceramide and reactive oxygen species. Cancer Res. Mar. 15, 2005;65(6):2422-32.

Rosen et al., Antiproliferative, cytotoxic and recovery effects in tumor-cell cultures treated with synthetic phospholipids. Int J Oncol. Sep. 1994;5(3):517-23.

Ruiter et al., Alkyl-lysophospholipids activate the SAPK/JNK pathway and enhance radiation-induced apoptosis. Cancer Res. May 15, 1999;59(10):2457-63.

Ruiter et al., Alkyl-lysophospholipids as anticancer agents and enhancers of radiation-induced apoptosis. Int J Radiat Oncol Biol Phys. Feb. 1, 2001;49(2):415-9.

Ruiter et al., Anti-cancer alkyl-lysophospholipids inhibit the phosphatidylinositol 3-kinase-Akt/PKB survival pathway. Anticancer Drugs. Feb. 2003;14(2):167-73.

Riiter et al., Submicromolar doses of alkyl-lysophospholipids induce rapid internalization, but not activation, of epidermal growth factor receptor and concomitant MAPK/ERK activation in A431 cells. Int J Cancer. Dec. 1, 2002;102(4):343-50.

Safa et al., Morphological changes and cytokine gene expression in tumor xenografts following treatment with the alkylphosphocholine hexadecylphosphocholine and perifosin. Drugs of Today, 1998, 34(Suppl. F):15-26.

Shoji et al., Effects of hexadecylphosphocholine on protein kinase C and TPA-induced differentiation of HL60 cells. Lipids. Feb. 1991:26(2):145-9.

Spruss et al., Antitumour activity of miltefosine alone and after combination with platinum complexes on MXT mouse mammary carcinoma models. J Cancer Res Clin Oncol. 1993;119(3):142-9.

Stekar et al., Opposite effect of miltefosine on the antineoplastic activity and haematological toxicity of cyclophosphamide. Eur J Cancer. 1995;31A(3):372-4.

Tai et al., Targeting MEK induces myeloma-cell cytotoxicity and inhibits osteoclastogenesis. Blood. Sep. 1, 2007;110(5):1656-63.

Tazzari et al., Synergistic proapoptotic activity of recombinant TRAIL plus the Akt inhibitor Perifosine in acute myelogenous leukemia cells. Cancer Res. Nov. 15, 2008;68(22):9394-403.

Unger et al., First-time-in-man and pharmacokinetic study of weekly oral perifosin in patients with solid tumours. Eur J Cancer. Mar. 2010;46(5):920-5.

van der Luit et al., A new class of anticancer alkylphospholipids uses lipid rafts as membrane gateways to induce apoptosis in lymphoma cells. Mol Cancer Ther. Aug. 2007;6(8):2337-45.

Van Ummersen et al., A phase I trial of perifosine (NSC 639966) on a loading dose/maintenance dose schedule in patients with advanced cancer. Clin Cancer Res. Nov. 15, 2004;10(22):7450-6.

Yijay and Gertz, Waldenström macroglobulinemia. Blood. Jun. 15, 2007;109(12):5096-103.

Vinall et al., Combination treatment of prostate cancer cell lines with bioactive soy isoflavones and perifosine causes increased growth arrest and/or apoptosis. Clin Cancer Res. Oct. 15, 2007;13(20):6204-16.

Vink et al., Lipid rafts and metabolic energy differentially determine uptake of anti-cancer alkylphospholipids in lymphoma versus carcinoma cells. Biochem Pharmacol. Nov. 15, 2007;74(10):1456-65 (Epub copy only).

Vink et al., Phase I and pharmacokinetic study of combined treatment with perifosine and radiation in patients with advanced solid tumours. Radiother Oncol. Aug. 2006;80(2):207-13.

Vink et al., Radiosensitization of squamous cell carcinoma by the alkylphospholipid perifosine in cell culture and xenografts. Clin Cancer Res. Mar. 1, 2006;12(5):1615-22.

Vink et al., Rationale and clinical application of alkylphospholipid analogues in combination with radiotherapy. Cancer Treat Rev. Apr. 2007;33(2):191-202.

Vink et al., Tumor and normal tissue pharmacokinetics of perifosine, an oral anti-cancer alkylphospholipid. Invest New Drugs. Aug. 2005;23(4):279-86.

Voltan et al., Perifosine plus nutlin-3 combination shows a synergistic anti-leukaemic activity. Br J Haematol. Mar. 2010;148(6):957-61.

Wolff M.E. (Ed.) "*Burger's Medicinal Chemistry and Drug Discovery*" 5$^{th}$ Edition, vol. 1: Principles and Practice. pp. 975-977, John Wiley & Sons, Inc. (1995).

Written Opinion for PCT application No. PCT/US2006/002988 (or PCT publication No. WO 2006/081452) dated Sep. 25, 2007.

Written Opinion for PCT application No. PCT/US2011/030800 (or PCT publication No. WO 2011/123691) dated Jul. 25, 2011.

Younes et al., Targeting the phosphatidylinositol 3-kinase pathway in multiple myeloma. Clin Cancer Res. Jul. 1, 2007;13(13):3771-5.

Zerp et al., Alkylphospholipids inhibit capillary-like endothelial tube formation in vitro: antiangiogenic properties of a new class of anti-tumor agents. Anticancer Drugs. Jan. 2008;19(1):65-75.

Bendell et al., "Randomized Placebo-Controlled Phase II Trial of Perifosine Plus Capecitabine as Second- or Third-Line Therapy in Patients With Metastatic Colorectal Cancer," *J. Clin. Oncol.* (2011), http://jco.ascopubs.org/cgi/doi/10.1200/JCO.2011.36.1980, 8 pages.

Babette Aicher, et al., Perifosine in Combination with Antimetabolites Induces Synergistic Effects on Cytotoxicity and Apoptosis in Human Colon, Multiple Myeloma, Breast, Renal, and Liver Tumor Cells, Abstract 203 (Poster) 22nd EORTC-NCI-AACR Symposium on Molecular Targets and Cancer Therapeutics, Nov. 17, 2010.

Babette Aicher, et al., Perifosine in Combination with Antimetabolites Induces Synergistic Effects on Cytotoxicity and Apoptosis in Human Colon, Multiple Myeloma, Breast, Renal, and Liver Tumor Cells, (Abstract) 22nd EORTC-NCI-AACR Symposium on Molecular Targets and Cancer Therapeutics, Nov. 17, 2010.

Johanna Bendell, et al., Randomized Phase II Study of Perifosine in Combination With Capecitabine (P-CAP) vs. Capecitabine Plus Placebo (CAP) in Patients With Second or Third Line Metastatic Colon Cancer (Mcrc): Updated Results (Poster), 2010 Gastrointestinal Cancers Symposium, held Jan. 22-24, 2010, Orlando FL.

Johanna Bendell, et al., Randomized Phase II Study of Perifosine in Combination With Capecitabine (P-CAP) vs. Capecitabine Plus Placebo (CAP) in Patients With Second or Third Line Metastatic Colon Cancer (Mcrc): Updated Results, (Abstract), 2010 Gastrointestinal Cancers Symposium, held Jan. 22-24, 2010, Orlando FL.
R. Birch, et al., Perifosine (KRX-0401)—An Active Agent in the Treatment of Patients with Advanced Sarcoma (Poster), 2007 ASCO Annual Meeting, held Jun. 1-5, 2007.
R. Birch, et al., Perifosine (P) as an active agent in the treatment of patients with advanced sarcoma, Journal of Clinical Oncology, 2007 ASCO Annual Meeting Proceedings Part I. vol. 25, No. 18S (Jun. 20 Supplement), 2007: 10059.
Rachel Midgley and David J Kerr, Capecitabine: have we got the dose right?, Nature Clinical Practice Oncology, pp. 17-24, Jan. 2009 vol. 6 No. 1.
D.C. Cho, et al. A phase II trial of perifosine in patients with advanced renal cell carcinoma (RCC) who have failed tyrosine kinase inhibitors (TKI), (Abstract), 2009 ASCO Annual Meeting, J Clin Oncol 27:15s, 2009 (suppl; abstr 5101).
D.C. Cho, et al. A phase II trial of perifosine in patients with advanced renal cell carcinoma (RCC) who have failed tyrosine kinase inhibitors (TKI), (Poster), 2009 ASCO Annual Meeting held May 29-Jun. 2, 2009, Orlando, Florida.
Daniel Cho, et al., Inhibition of Glycogen Synthase Kinase 3β (GSK3β) Enhances the In Vitro Activity of the Akt Inhibitor Perifosine in Renal Cell Carcinoma (RCC) Cell Lines (Poster), 98th AACR Annual Meeting—held Apr 14-18, 2007; Los Angeles, CA.
Daniel Cho, et al., Inhibition of Glycogen Synthase Kinase 3β (GSK3β) Enhances the In Vitro Activity of the Akt Inhibitor Perifosine in Renal Cell Carcinoma (RCC) Cell Lines (Abstract No. 1823), 98th AACR Annual Meeting—held Apr 14-18, 2007; Los Angeles, CA.
Diana Cirstea, M.D., et al., Combination of Nab-Rapamycin and Perifosine Induces Synergistic Cytotoxicity and Antitumor Activity Via Autophagy and Apoptosis in Multiple Myeloma (MM) (Poster), American Society of Hematology (ASH) 50th Annual Meeting and Exposition, held Dec. 6-9, 2008; San Francisco, California.
Diana Cirstea, M.D., et al., Combination of Nab-Rapamycin and Perifosine Induces Synergistic Cytotoxicity and Antitumor Activity Via Autophagy and Apoptosis in Multiple Myeloma (MM) (Abstract), American Society of Hematology (ASH) 50th Annual Meeting and Exposition, held Dec. 6-9, 2008; San Francisco, California.
A. P. Conley, et al., A randomized phase II study of perifosine (P) plus imatinib for patients with imatinib-resistant gastrointestinal stromal tumor (GIST) (Abstract), 2009 ASCO Annual Meeting, J Clin Oncol 27:15s, 2009 (suppl; abstr 10563), held May 29 through Jun. 2, 2009, Orlando, FL.
A. P. Conley, et al., A randomized phase II study of perifosine (P) plus imatinib for patients with imatinib-resistant gastrointestinal stromal tumor (GIST) (Poster), 2009 ASCO Annual Meeting, held May 29 through Jun. 2, 2009, Orlando, FL.
Irene M. Ghobrial, et al., Phase II Trial of the Novel Oral Akt Inhibitor Perifosine in Relapsed and/or Refractory Waldenström Macroglobulinemia (Poster), 2007 ASH Annual Meeting, held Dec. 8-11, 2007, Atlanta, GA.
Irene M. Ghobrial, et al., Phase II Trial of Perifosine (KRX-0401) in Relapsed and/or Refractory Waldenström Macroglobulinemia: Preliminary Results (Abstract), Blood (ASH Annual Meeting Abstracts), Nov 2007; 110: 4493.
F. A. Greco, et al., Safety and pharmacokinetic (PK) study of perifosine plus capecitabine (PCAP) in patients (pts) with refractory metastatic colorectal cancer (mCRC), J Clin Oncol 28, 2010 (suppl; abstr e14086), 2010 ASCO Annual Meeting.
Bryan Hennessy, et al., Perifosine accumulates preferentially in tumor tissues: Correlation between accumulation in tumor tissue and inhibition of cell proliferation and tumor growth (Poster), AACR-NCI-EORTC International Conference: Molecular Targets and Cancer Therapeutics—held Oct 22-26, 2007; San Francisco, CA.
Bryan Hennessy, et al., Perifosine accumulates preferentially in tumor tissues: Correlation between intratumoral accumulation and inhibition of cell proliferation and tumor growth (Abstract) AACR Meeting Abstracts, Oct. 2007; 2007: C178, AACR-NCI-EORTC International Conference: Molecular Targets and Cancer Therapeutics—held Oct. 22-26, 2007; San.Francisco, CA.

Hoff P., et al., O-0017. Subset Analysis Of 5-Fu Refractory Patients From A Randomized PH II Study Of Perifosine 1 Capecitabine (P-Cap) vs. Placebo 1 Capecitabine (Cap) In Patients With 2nd Or 3rd Line Metastatic CRC (Abstract), 12th World Congress on Gastrointestinal Cancer, Barcelona, Spain, held Jun. 30-Jul. 2, 2010.
Paulo Hoff, et al., Subset Analysis Of 5-Fu Refractory Patients From The Final Results Of A Randomized Phase II Study Of Perifosine In Combination With Capecitabine (P-Cap) vs. Placebo Plus Capecitabine (Cap) In Patients With Second Or Third Line Metastatic Colorectal Cancer (mCRC) (Poster), 12th World Congress on Gastrointestinal Cancer, Barcelona, Spain, held Jun. 30-Jul. 2, 2010.
A. Huston, MD, et al., Combination of the Akt Inhibitor Perifosine with the Hsp90 Inhibitor 17-(dimethylaminoethylamino)-17-demethoxygeldanamycin (17-DMAG) has Synergistic Activity in Multiple Myeloma (Poster) 2005 ASH Annual Meeting, held Dec. 10-13, 2005; Atlanta, Georgia.
Alissa Huston, MD, et al., Combination of the AKT Inhibitor Perifosine with the HSP90 Inhibitor 17-(Dimethylaminoethylamino)-17-Demethoxygeldanamycin (17-DMAG) Has Synergistic Activity in Multiple Myeloma (MM) (Abstract) Blood (ASH Annual Meeting Abstracts) 2005 106: Abstract 1592.
A. Huston, MD, et al., The Role of the Akt Inhibitor Perifosine in Migration and Adhesion in Multiple Myeloma A (Poster) 2005 ASH Annual Meeting, held Dec. 10-13, 2005; Atlanta, Georgia.
Alissa Huston, MD, et al., The Role of the AKT Inhibitor Perifosine in Migration and Adhesion in Multiple Myeloma (MM) (Abstract) Blood (ASH Annual Meeting Abstracts) 2005 106: Abstract 2509.
A. Huston, MD, et al., Proteomic Analysis Identifies Differences in Multiple Myeloma Cells Sensitive and Resistant to Akt Inhibition (Poster) 2005 ASH Annual Meeting held Dec. 10-13, 2005; Atlanta, Georgia.
Alissa Huston, MD, et al., Proteomic Analysis Identifies Differences in Multiple Myeloma (MM) Cells Sensitive and Resistant to AKT Inhibition (Abstract) Blood (ASH Annual Meeting Abstracts) 2005 106: Abstract 3402.
Andrzej Jakubowiak, et al., A Multiple Myeloma Research Consortium (MMRC) Multicenter Phase I Trial of Perifosine (Krx-0401) In Combination With Lenalidomide And Dexamethasone In Patients With Relapsed Or Refractory Multiple Myeloma (MM): Updated Results Introduction (Poster) 2008 Blood (ASH Annual Meeting Abstracts) 2008 112: Abstract 3691.
Hyo Song Kim, et al., Evaluation Of Anticancer Drug Sensitivity And Gene Expression Patterns Of A Novel Akt Inhibitor, Perifosine In Gastric Cancer (Poster) 2011 AACR Annual Meeting held Apr. 2-6, 2011.
Tae Soo Kim et al., Presentation Title: Antitumor activity of novel Akt inhibitor, perifosine in gastric cancer cell lines (Abstract No. 1965) 2011 AACR Annual Meeting held Apr. 2-6, 2011.
Andrew Lassman, et al., Clinical And Molecular-Metabolic Phase Ii Trial Of Perifosine For Recurrent/Progressive Malignant Glioma (Abstract) 12th Annual Meeting of the Society for Neurooncology held Nov. 15-18, 2007.
Ab Lassman, et al., Phase II Trial of Perifosine for Recurrent Malignant Glioma (Poster) 12th Annual Meeting of The Society For Neurooncology held Nov. 15-18, 2007.
Zhijie Li, et al., Perifosine, as a single agent, inhibits neuroblastoma tumor cell growth in vitro and in vivo (Poster) 2009 AACR Annual Meeting held Apr. 18-22, 2009, Denver, CO.
Zhijie Li, et al, Perifosine, as a single agent, inhibits neuroblastoma tumor cell growth in in vitro and in vivo preclinical models (Abstract #3205) 2009 AACR Annual Meeting held Apr. 18-22, 2009, Denver, CO.
Zhijie Li, et al., Neuroblastoma tumors with different ALK mutations are sensitive to Perifosine (Poster) 101st Annual Meeting of the American Association for Cancer Research (AACR), Washington, DC. Apr. 21, 2010.
Zhijie Li, et al., Presentation Title: Neuroblastoma tumors with different ALK mutations are sensitive to Perifosine (Abstract No. 5248) 101st Annual Meeting of the American Association for Cancer Research (AACR), Washington, DC. Apr. 21, 2010.
Zhijie Li, et al., Perifosine, an Akt inhibitor, sensitizes Neuroblastoma to etoposide treatment (Poster) 2008.

Enrique Poradosu, et al., Perifosine selectively inhibits binding of Akt PH domain to Ptdlns(3,4)P2 (Abstract #1645) 2007 AACR Annual Meeting held Apr. 14-18, 2007, Los Angeles, CA.

Enrique Poradosu, et al., Identification of Pharmacodynamic Markers for Effects of Perifosine (KRX0401) on the PI3K Pathway in vivo (Poster) 2005 AACR-NCI-EORTC International Conference on Molecular Targets and Cancer Therapeutics: Discovery, Biology, and Clinical Applications held Nov. 14-18, 2005.

Enrique Poradosu, et al., Identification of Pharmacodynamic Markers for Effects of Perifosine (KRX0401) on the PI3K Pathway in vivo (Abstract A194) 2005 AACR-NCI-EORTC International Conference on Molecular Targets and Cancer Therapeutics: Discovery, Biology, and Clinical Applications held Nov. 14-18, 2005.

Enrique Poradosu, Ph.D., Perifosine: An Akt Inhibitor in Clinical Trials, oral presentation at 2007 AACR Meeting.

Donald Richards, et al., Final Results Of A Randomized Phase II Study Of Perifosine In Combination With Capecitabine (P-CAP) vs. Placebo Plus Capecitabine (CAP) In Patients With Second Or Third Line Metastatic Colorectal Cancer (mCRC) (Poster) 2010 ASCO Annual Meeting held Jun. 4-8, 2010—Chicago, IL; J Clin Oncol 28:15s, 2010 (suppl; abstr 3531).

Paul Richardson, MD, et al., Phase I/II Results of a Multicenter Trial of Perifosine (KRX-0401) + Bortezomib in Patients with Relapsed or Relapsed/Refractory Multiple Myeloma Who Were Previously Relapsed From or Refractory to Bortezomib; (Oral Session *Novel Therapies for Myeloma and Related Disorders*) Blood (ASH Annual Meeting Abstracts) 2008 112: Abstract 870.

Paul Richardson, MD, et al., A Multicenter Phase I/Ii Trial Of Perifosine (Krx-0401) + Bortezomib In Relapsed Or Relapsed/Refractory Multiple Myeloma Patients Previously Treated With Bortezomib: Phase I Results (Poster) Dec. 8, 2007 at the 49th Annual Meeting of the American Society of Hematology.

Paul Richardson, MD, et al., Phase I/II Report from a Multicenter Trial of Perifosine (KRX-0401) + Bortezomib in Patients with Relapsed or Relapsed/Refractory Multiple Myeloma Previously Treated with Bortezomib (Abstract) Blood (ASH Annual Meeting Abstracts) 2007 110: Abstract 1170.

Paul Richardson, MD, et al., A Phase I/II Study Evaluating the Safety and Efficacy of Perifosine + Bortezomib (+/− Dexamethasone) for Patients with Relapsed or Relapsed / Refractory Multiple Myeloma who were Previously Treated with Bortezomib (Power Point Presentation) 2008 ASH Meeting.

Paul Richardson, MD, et al., Perifosine in Combination with Bortezomib and Dexamethasone Extends Progression-Free Survival and Overall Survival in Relapsed/Refractory Multiple Myeloma Patients Previously Treated with Bortezombib: Updated Phase I/II Trial Results (Abstract No. 1869) (Poster Board I-894) Blood (ASH Annual Meeting Abstracts) 2009, 114: Abstract 1869.

Paul Richardson, MD, et al., Perifosine Plus Bortezomib And Dexamethasone Extends Progression-Free Survival And Overall Survival In Relapsed / Refractory Multiple Myeloma Patients Previously Treated With Bortezomib: Updated Results Of The Phase I/Ii Trial (Poster), 2009 ASH Annual Meeting held Dec. 5-8, 2009, New Orleans.

Alexandros S. Ardavanis, et al., Salvage Treatment with Single-agent Capecitabine in Patients with Heavily Pretreated Advanced Colorectal Cancer, Anticancer Research 26: 1669-1672 (2006).

N. J. Vogelzang, et al., Phase II Study Of Perifosine In Metastatic RCC (Clear And Non-Clear) Progressing After One Prior Therapy (Rx) With a VEGF Receptor Inhibitor (Abstract), 2009 ASCO Genitourinary Cancers Symposium held Feb. 26-28, 2009, Orlando, Florida.

Nicholas J. Vogelzang, et al., Phase II Study Of Perifosine In Metastatic Renal Cell Carcinoma (Clear And Non-Clear) Progressing After One Prior Therapy (Rx) With A VEGF Receptor Inhibitor (Poster) 2009 ASCO Genitourinary Cancers Symposium held Feb. 26-28, 2009, Orlando, Florida.

N. J. Vogelzang, et al., Phase II Study Of Perifosine In Metastatic Renal Cell Carcinoma (RCC) Progressing After Prior Therapy (Rx) With a VEGF Receptor Inhibitor (Abstract) 2009 ASCO Annual Meeting, J Clin Oncol 27:15s, 2009 (suppl; abstr 5034).

Nicholas J. Vogelzang, et al., Phase II Study Of Perifosine In Metastatic Renal Cell Carcinoma Progressing Either After One Prior Therapy (Rx) With A VEGF Receptor Inhibitor or A VEGF And An mTOr Inhibitor (Poster) 2009 ASCO Annual Meeting held May 29-Jun. 2, 2009, Orlando, Florida.

Ra Sasha Vukelja, et al., Randomized Phase II Study Of Perifosine In Combination With Capecitabine vs. Capecitabine Alone In Patients With Second Or Third Line Metastatic Colon Cancer (Poster) 2009 ASCO Annual Meeting held May 29-Jun. 2, 2009 in Orlando, Florida.

S. Vukelja, et al., Randomized phase II study of perifosine in combination with capecitabine versus capecitabine alone in patients with second- or third-line metastatic colon cancer, (Abstract No: 4081), 2009 ASCO Annual Meeting, J Clin Oncol 27:15s, 2009 (suppl; abstr 4081).

Apr. 2, 2012 Keryx Press Release.

Pending Claims for U.S. Appl. No. 12/798,267, 2010.

Pending Claims for U.S. Appl. No. 12/751,608, 2010.

Pending Claims for U.S. Appl. No. 12/751,454, 2010.

Pending Claims for U.S. Appl. No. 10/632,187, 2003.

Notice of Allowability for U.S. Appl. No. 10/632,187, 2003.

* cited by examiner

PERIFOSINE AND CAPECITABINE AS A COMBINED TREATMENT FOR CANCER

This application claims the benefit under 35 U.S.C. §119 (e) of U.S. Provisional Application No. 61/319,315, filed Mar. 31, 2010, which is incorporated herein by reference in its entirety.

FIELD

The present disclosure relates to the field of pharmacology, and more particularly, but not exclusively, to combination therapies and treatment regimens combining an alkylphospholipid and a fluoropyrimidine, which can be used to treat cancer.

BACKGROUND

Alkylphospholipids represent a new class of lipid-related compounds that exhibit anticancer activity. Alkylphospholipids exhibit very unique patterns of in vitro cell growth inhibition that are distinctly different from those of most cytotoxic agents, by accumulating in cell membranes and modifying cell signaling pathways [Arthur and Bittman, *Biochim Biophys Acta* 1998, 1390:85-102].

Miltefosine is an alkylphospholipid licensed in Europe as a topical application for treatment of cutaneous metastases from breast cancer. It is also used in an oral formulation to treat leishmaniasis. Miltefosine exhibits gastrointestinal toxicity.

Perifosine (1,1-dimethyl-4-[[(octadecyloxy)hydroxyphosphinyl]oxy]-piperidinium inner salt) is a synthetic alkylphospholipid identified as a more active and better tolerated alternative to miltefosine [Hilgard et al. *Eur J Cancer* 1997, 33:442-446]. Perifosine exhibited marked activity in animal and human tumor cell lines resistant to standard chemotherapeutic agents, with relative sparing of normal cells. Oral administration of perifosine was shown to be effective against tumors in several in vivo animal models.

Perifosine has been shown to inhibit or otherwise modify signaling through a number of different signal transduction pathways, including, for example, Akt, p21 and JNK.

Akt activation has been shown to be important in a number of different cancer types, particularly cancers characterized by a poor prognosis. Perifosine blocks phosphorylation of Akt, thereby inhibiting activation of Akt [Kondapaka et al., *Mol Cancer Ther* 2003, 2:1093-1103; Ruiter et al., *Anticancer Drugs* 2003, 14:167-173].

Perifosine also stimulates the SAPK/JNK cascade, which normally promotes apoptosis following unusual stress. Perifosine may increase levels of apoptosis induced by radiotherapy [Verheij et al., *American Society of Clinical Oncology* 2004, New Orleans La.].

Capecitabine, which is marketed as Xeloda®, is an orally administered fluoropyrimidine that is converted to 5-fluorouracil in tumors. Capecitabine is indicated for the following treatments:

first-line treatment of metastatic colorectal carcinoma;

adjuvant treatment in patients with Dukes' C colon cancer who have undergone complete resection of the primary tumor;

treatment of metastatic breast cancer in combination with docetaxel, after failure of anthracycline-containing chemotherapy; and monotherapy for metastatic breast cancer resistant to paclitaxel, when an anthracycline-containing regimen is not indicated.

The Xeloda® Prescribing Information [1999: Roche Inc.], which is incorporated herein by reference in its entirety, lists recommendations for capecitabine administration and relevant data.

The recommended dose of capecitabine for all of the above-mentioned indications is 1250 mg/m$^2$, administered orally twice daily (i.e., 2500 mg/m$^2$ total daily dose) in 3-week cycles consisting of administration for 2 weeks followed by a 1-week rest period. Upon appearance of Grade 2, 3 or 4 toxicity, it is recommended to interrupt capecitabine treatment to resolve the toxicity to Grade 0 or 1, after which capecitabine treatment may be resumed. Resumption of capecitabine treatment following Grade 3 toxicity is recommended to be at 75% of the original dose. Resumption of capecitabine treatment following Grade 4 toxicity, if performed, is recommended to be at 50% of the original dose.

Adverse events or side effects caused in patients receiving capecitabine are similar to those in patients receiving 5-fluorouracil, and include gastrointestinal disorders (e.g., diarrhea, nausea, stomatitis, vomiting, abdominal pain), hand-foot syndrome, EKG changes, myocardial infarction, angina, neutropenia, anemia, thrombocytopenia and hyperbilirubinemia.

Capecitabine is contraindicated in patients with hypersensitivity to 5-fluorouracil, in patients with dihydropyrimidine dehydrogenase deficiency and in patients with severe renal impairment. Dose reduction is recommended for patients with moderate renal impairment. It is recommended to avoid pregnancy and nursing when receiving capecitabine. Anticoagulant doses may need to be modified when receiving capecitabine.

Peak capecitabine blood level occurs about 1.5 hours after administration, with peak 5-fluorouracil level occurring slightly later (2 hours). Food reduces both the rate and extent of capecitabine absorption. The elimination half-life of both capecitabine and 5-fluorouracil is about ¾ of an hour.

Colorectal cancer is one of the leading causes of cancer-related death in the Western world. Treatment of colorectal cancer often utilizes 5-fluorouracil as a chemotherapeutic agent. The FOLFIRI and FOLFOX regimens combine 5-fluorouracil with leucovorin and either irinotecan (FOLFIRI) or oxaliplatin (FOLFOX). Tumor resistance to 5-fluorouracil may be mediated by upregulation of NF-κB [Voboril et al., *J Surg Res* 2004, 120:178-188]. Bevacizumab, cetuximab and panitumumab are also used either in combination with chemotherapy or as a single agent for treating colorectal cancer.

Nearly 40% of colorectal tumors have alterations in the PI3/Akt pathway, including activating mutations in p110α (a PI3-kinase subunit) or loss of PTEN (a tumor suppressor protein which regulates the PIS/Akt pathway) [Brugge et al., *Cancer Cell* 2007, 12:104-107; Rychahou et al., *PNAS* 2008, 105:20315-20320; Sawai et al., *BMC Gastroenterol* 2008, 8:56].

U.S. Patent Application No. 2004/0097470 describes a use of alkylphosphocholines in combination with antitumor medicaments for the treatment of oncoses.

International Patent Application PCT/DE99/03952 (published as WO 00/033917) describes a combination of an antineoplastic alkylphospholipid with an antiestrogen such as tamoxifen.

International Patent Application PCT/US2006/002988 (published as WO 06/081452) describes methods of treating cancer by co-administration of perifosine and a second chemotherapeutic agent, such as paclitaxel, docetaxel, gemcitabine and trastuzumab.

Additional background art includes Hilgard et al., *Advances in Experimental Medicine and Biology* 1996, 416: 157-164; Hilgard et al., *Cancer Chemotherapy and Pharma-* cology 1993, 32:90-95; Spruss et al., *J. Cancer Research and Clinical Oncology* 1993, 119:142-149; Berkovic et al., *Leukemia* 1997, 11:2079-2086; and Georgieva et al., *Cancer Letters* 2002, 182:163-174.

SUMMARY

The present inventors have now unexpectedly uncovered that a treatment regimen which combines capecitabine and perifosine enables using doses of capecitabine that are lower than those currently utilized in treating the above-indicated medical conditions, while maintaining the therapeutic efficacy of capecitabine, and moreover, while improving the time-to-tumor progression and overall survival.

According to an aspect of some embodiments of the present disclosure there is provided a method of treating cancer in a subject in need thereof, the method comprising administering to the subject a therapeutically effective amount of perifosine and a therapeutically effective amount of capecitabine, wherein the therapeutically effective amount of perifosine ranges from 10 mg per day to 200 mg per day and the therapeutically effective amount of capecitabine ranges from 1500 mg/m² per day to 1800 mg/m² per day.

According to an aspect of some embodiments of the present disclosure there is provided a method of treating cancer in a subject in need thereof, the method comprising administering to the subject a therapeutically effective amount of perifosine and a therapeutically effective amount of capecitabine, wherein the therapeutically effective amount of perifosine ranges from 10 mg per day to 200 mg per day and the therapeutically effective amount of capecitabine ranges from 1850 mg/m² per day to 2150 mg/m² per day.

According to an aspect of some embodiments of the present disclosure there is provided a pharmaceutical composition comprising perifosine, the pharmaceutical composition being packaged in a packaging material and identified, in or on the packaging material, for use in combination with a therapeutically effective amount of capecitabine, for the treatment of cancer, the pharmaceutical composition being formulated for oral administration.

According to an aspect of some embodiments of the present disclosure there is provided a pharmaceutical composition unit dosage form comprising perifosine and capecitabine, the composition comprising from 10 mg to 200 mg perifosine and from 2500 mg to 3200 mg capecitabine.

According to an aspect of some embodiments of the present disclosure there is provided a pharmaceutical composition unit dosage form comprising perifosine and capecitabine, the composition comprising from 10 mg to 200 mg perifosine and from 3100 mg to 3800 mg capecitabine.

According to an aspect of some embodiments of the present disclosure there is provided a pharmaceutical composition unit dosage form comprising perifosine and capecitabine, the composition comprising from 10 mg to 200 mg perifosine and from 1250 mg to 1600 mg capecitabine, and the composition being identified for use in combination with a unit dosage form which comprises a therapeutically effective amount of capecitabine.

According to an aspect of some embodiments of the present disclosure there is provided a pharmaceutical composition unit dosage form comprising perifosine and capecitabine, the composition comprising from 10 mg to 200 mg perifosine and from 1550 mg to 1900 mg capecitabine, and the composition being identified for use in combination with a unit dosage form which comprises a therapeutically effective amount of capecitabine.

According to some embodiments of the disclosure, the therapeutically effective amount of perifosine ranges from 10 mg per day to 100 mg per day.

According to some embodiments of the disclosure, the therapeutically effective amount of perifosine ranges from 40 mg per day to 60 mg per day.

According to some embodiments of the disclosure, the therapeutically effective amount of perifosine is 50 mg per day.

According to some embodiments of the disclosure, administering perifosine is effected once per day.

According to some embodiments of the disclosure, administering the capecitabine is effected twice per day.

According to some embodiments of the disclosure, the therapeutically effective amount of capecitabine is 1650 mg/m² per day.

According to some embodiments of the disclosure, administering the capecitabine comprises administering twice per day a dosage unit form which comprises 825 mg/m² capecitabine.

According to some embodiments of the disclosure, the therapeutically effective amount of capecitabine is 2000 mg/m² per day.

According to some embodiments of the disclosure, administering the capecitabine comprises administering twice per day a dosage unit form which comprises 1000 mg/m² capecitabine.

According to some embodiments of the disclosure, the pharmaceutical composition described hereinabove is a unit dosage form which comprises from 10 mg to 200 mg perifosine.

According to some embodiments of the disclosure, the unit dosage form comprises from 40 mg to 60 mg perifosine.

According to some embodiments of the disclosure, the unit dosage form comprises 50 mg perifosine.

According to some embodiments of the disclosure, the pharmaceutical composition described herein is identified for administration once per day.

According to some embodiments of the disclosure, the therapeutically effective amount of capecitabine in the pharmaceutical composition described hereinabove is in a range of from 1200 mg/m² per day to 2500 mg/m² per day.

According to some embodiments of the disclosure, the therapeutically effective amount of capecitabine is in a range of from 1850 mg/m² per day to 2150 mg/m² per day.

According to some embodiments of the disclosure, the therapeutically effective amount of capecitabine is in a range of from 1500 mg/m² per day to 1800 mg/m² per day.

According to some embodiments of the disclosure, the unit dosage form is formulated so as to exhibit an immediate release of the perifosine and a first portion of the capecitabine in the unit dosage form, and a delayed release of a second portion of the capecitabine in the unit dosage form, each of the first portion and the second portion of the capecitabine comprising from 1250 mg to 1600 mg capecitabine.

According to some embodiments of the disclosure, the unit dosage form is formulated so as to exhibit an immediate release of a first portion of the capecitabine in the unit dosage form, and a delayed release of the perifosine and a second portion of the capecitabine in the unit dosage form, each of the first portion and the second portion of the capecitabine comprising from 1250 mg to 1600 mg capecitabine.

According to some embodiments of the disclosure, the unit dosage form is formulated so as to exhibit an immediate release of the perifosine and a first portion of the capecitabine in the unit dosage form, and a delayed release of a second portion of the capecitabine in the unit dosage form, each of the first portion and the second portion of the capecitabine comprising from 1550 mg to 1900 mg capecitabine.

According to some embodiments of the disclosure, the unit dosage form is formulated so as to exhibit an immediate release of a first half of the capecitabine in the unit dosage form, and a delayed release of the perifosine and a second half of the capecitabine in the unit dosage form, each of the first portion and the second portion of the capecitabine comprising from 1550 mg to 1900 mg capecitabine.

According to some embodiments of the disclosure, the pharmaceutical composition unit dosage form described hereinabove is identified for administration once per day.

According to some embodiments of the disclosure, the therapeutically effective amount of capecitabine is in a range of from 1250 mg to 1600 mg capecitabine.

According to some embodiments of the disclosure, the pharmaceutical composition unit dosage form described herein is identified for use by administration of the pharmaceutical composition unit dosage form once per day in combination with administration of the unit dosage form of capecitabine once per day, wherein administration of the pharmaceutical composition unit dosage form and administration of the unit dosage form of capecitabine are at least 8 hours apart.

According to some embodiments of the disclosure, the unit dosage form of capecitabine comprises capecitabine in a range of from 1550 mg to 1900 mg capecitabine.

According to some embodiments of the disclosure, the pharmaceutical composition unit dosage form described hereinabove is packaged in a packaging material and identified for use, in or on the packaging material, for use in the treatment of cancer.

According to some embodiments of the disclosure, the cancer is a colorectal cancer.

According to some embodiments of the disclosure, the method described hereinabove is for treating a subject that has received a prior chemotherapy treatment.

According to some embodiments of the disclosure, the pharmaceutical composition described hereinabove is for treating a subject that has received a prior chemotherapy treatment.

According to some embodiments of the disclosure, the pharmaceutical composition unit dosage form described hereinabove is for treating a subject that has received a prior chemotherapy treatment.

According to some embodiments of the disclosure, the prior chemotherapy treatment comprises administration of a chemotherapeutic agent selected from the group consisting of paclitaxel, an anthracycline, a fluoropyrimidine, irinotecan, oxaliplatin, bevacizumab, cetuximab and panitumumab.

According to some embodiments of the disclosure, the method described hereinabove is for treating a cancer characterized by an acquired resistance to a chemotherapeutic agent.

According to some embodiments of the disclosure, the pharmaceutical composition described hereinabove is for treating a cancer characterized by an acquired resistance to a chemotherapeutic agent.

According to some embodiments of the disclosure, the pharmaceutical composition unit dosage form described hereinabove is for treating a cancer characterized by an acquired resistance to a chemotherapeutic agent.

According to some embodiments of the disclosure, the cancer is characterized by an acquired resistance to a chemotherapeutic agent selected from the group consisting of paclitaxel, an anthracycline, a fluoropyrimidine, irinotecan, oxaliplatin, bevacizumab, cetuximab and panitumumab.

According to some embodiments of the disclosure, the method described hereinabove is for treating a subject characterized as intolerant to a prior chemotherapy treatment.

According to some embodiments of the disclosure, the pharmaceutical composition described hereinabove is for treating a subject characterized as intolerant to a prior chemotherapy treatment.

According to some embodiments of the disclosure, the pharmaceutical composition unit dosage form described hereinabove is for treating a subject characterized as intolerant to a prior chemotherapy treatment.

According to some embodiments of the disclosure, the prior chemotherapy treatment comprises administering to the subject a chemotherapeutic agent selected from the group consisting of a fluoropyrimidine and oxaliplatin.

According to some embodiments of the disclosure, the cancer is metastatic.

Unless otherwise defined, all technical and/or scientific terms used herein have the same meaning as commonly understood by one of ordinary skill in the art to which the disclosure pertains. Although methods and materials similar or equivalent to those described herein can be used in the practice or testing of embodiments of the disclosure, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the disclosure are herein described, by way of example only, with reference to the accompanying drawings. With specific reference now to the drawings in detail, it is stressed that the particulars shown are by way of example and for purposes of illustrative discussion of embodiments of the disclosure. In this regard, the description taken with the drawings makes apparent to those skilled in the art how embodiments of the disclosure may be practiced.

In the drawings.

DETAILED DESCRIPTION

The present disclosure, in some embodiments thereof, relates to the field of pharmacology, and more particularly, but not exclusively, to a treatment regimen combining an alkylphospholipid and a fluoropyrimidine, which can be efficiently used to treat cancer.

The principles and operation of the present disclosure may be better understood with reference to the figures and accompanying descriptions.

Before explaining at least one embodiment of the disclosure in detail, it is to be understood that the disclosure is not limited in its application to the details set forth in the following description or exemplified by the Examples. The disclosure is capable of other embodiments or of being practiced or carried out in various ways. Also, it is to be understood that the phraseology and terminology employed herein is for the purpose of description and should not be regarded as limiting.

While perifosine has shown considerable promise as an anti-cancer agent in various laboratory models, the present inventors have studied its effect in combination therapy and have surprisingly uncovered that a combined treatment of perifosine and capecitabine results in a synergistic effect in the treatment of colorectal cancer.

Thus, the present inventors have studied the safety and efficacy of perifosine in subjects receiving various standard chemotherapies along with perifosine. The protocols of these assays are described in detail in the Examples section that follows.

Based on the data obtained in the clinical studies conducted, the present inventors have uncovered the unexpected result that perifosine is particularly effective when co-administered with capecitabine, and that there is a synergistic effect between perifosine and capecitabine. The present inventors have further uncovered that when capecitabine is combined with perifosine, capecitabine can be utilized in lower doses than the doses usually prescribed for colorectal cancer patients, while still exhibiting at least the same, if not enhanced, therapeutic effect. The present inventors have further studied the safety and efficacy of co-administration of perifosine and capecitabine using various doses, in order to determine preferred doses for such a treatment.

The recommended daily dose of capecitabine (2500 mg/m² per day) has been found to cause numerous adverse side effects, including gastrointestinal disorders, hand-foot syndrome, EKG changes, myocardial infarction, angina, neutropenia, anemia, thrombocytopenia and hyperbilirubinemia. The adverse side effects at this dose are often quite severe and may endanger the life of the patient. However, simply reducing the dose of capecitabine may detrimentally reduce the therapeutic effect of the capecitabine, thereby reducing the probability of a cancer patient surviving the cancer.

There is therefore a need for a way to reduce a dose of capecitabine while maintaining the therapeutic anti-cancer effect of capecitabine.

Figure 1:
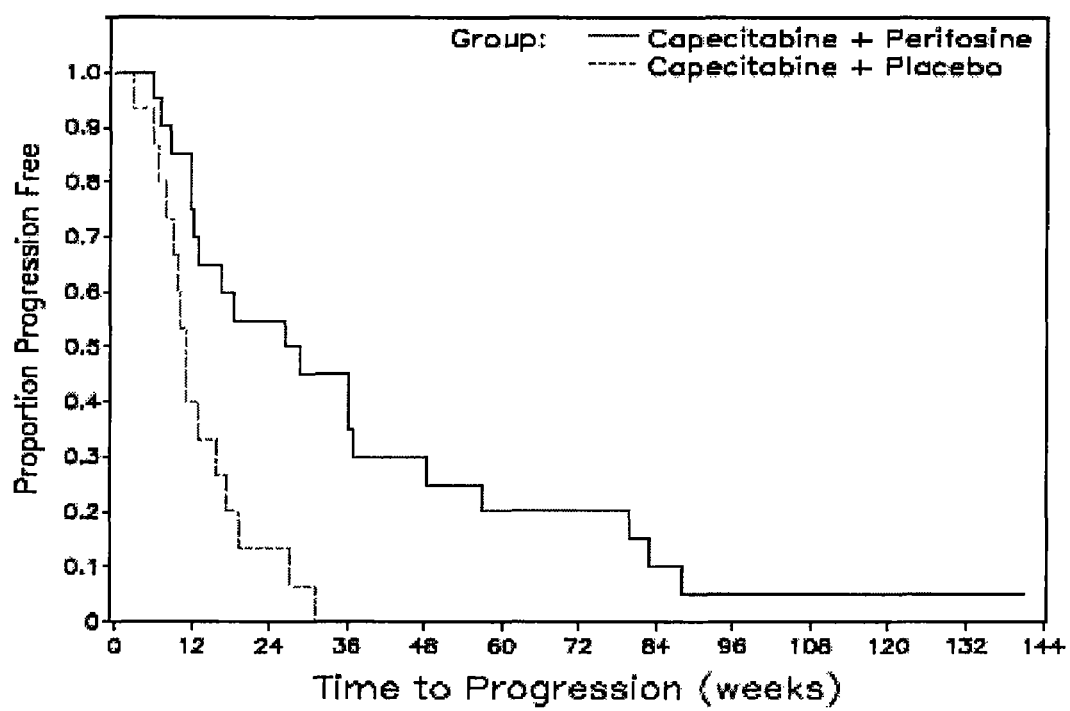
FIG. 1 is a graph showing the proportion of tested metastatic colorectal cancer patients who were progression-free, as a function of time, when administered 1650 mg/m$^2$ per day capecitabine (days 1-14 every 21 days) with 50 mg per day perifosine or 1650 mg/m$^2$ per day capecitabine (days 1-14 every 21 days) with a placebo.
Figure 2:
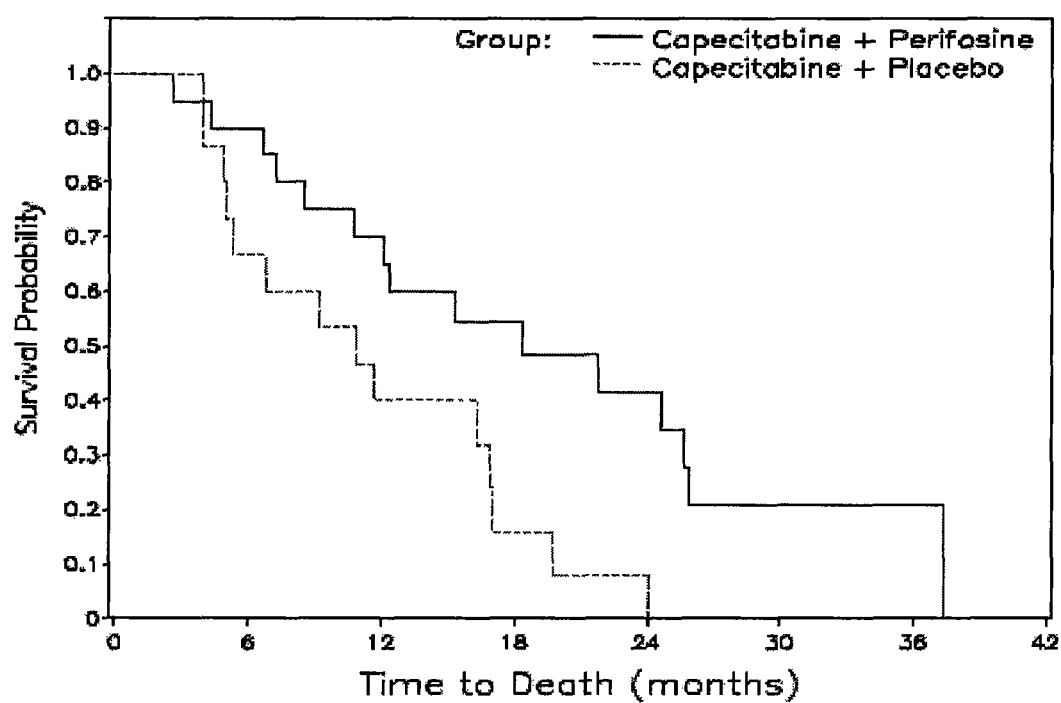
FIG. 2 is a graph showing the survival probability for tested metastatic colorectal cancer patients, as a function of time, when administered 1650 mg/m$^2$ per day capecitabine (days 1-14 every 21 days) with 50 mg per day perifosine or 1650 mg/m$^2$ per day capecitabine (days 1-14 every 21 days) with a placebo.

Referring now to the drawings, FIG. 1 shows that perifosine significantly increased the proportion of tested metastatic colorectal cancer patients who were progression-free, among patients treated with 1650 mg/m² capecitabine per day. FIG. 2 shows that perifosine significantly improved the survival probability for tested metastatic colorectal cancer patients being treated with 1650 mg/m² capecitabine per day.

Figure 3:
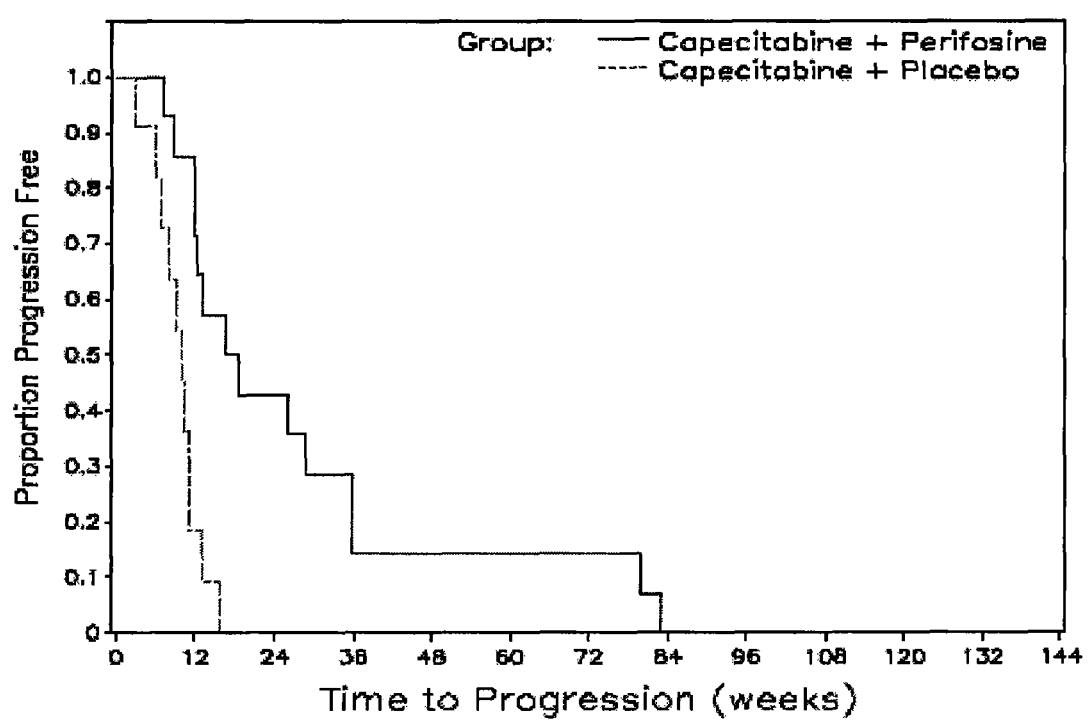
FIG. 3 is a graph showing the proportion of tested 5-fluorouracil-refractory metastatic colorectal cancer patients who were progression-free, as a function of time, when administered 1650 mg/m$^2$ per day capecitabine (days 1-14 every 21 days) with 50 mg per day perifosine or 1650 mg/m$^2$ per day capecitabine (days 1-14 every 21 days) with a placebo.
Figure 4:
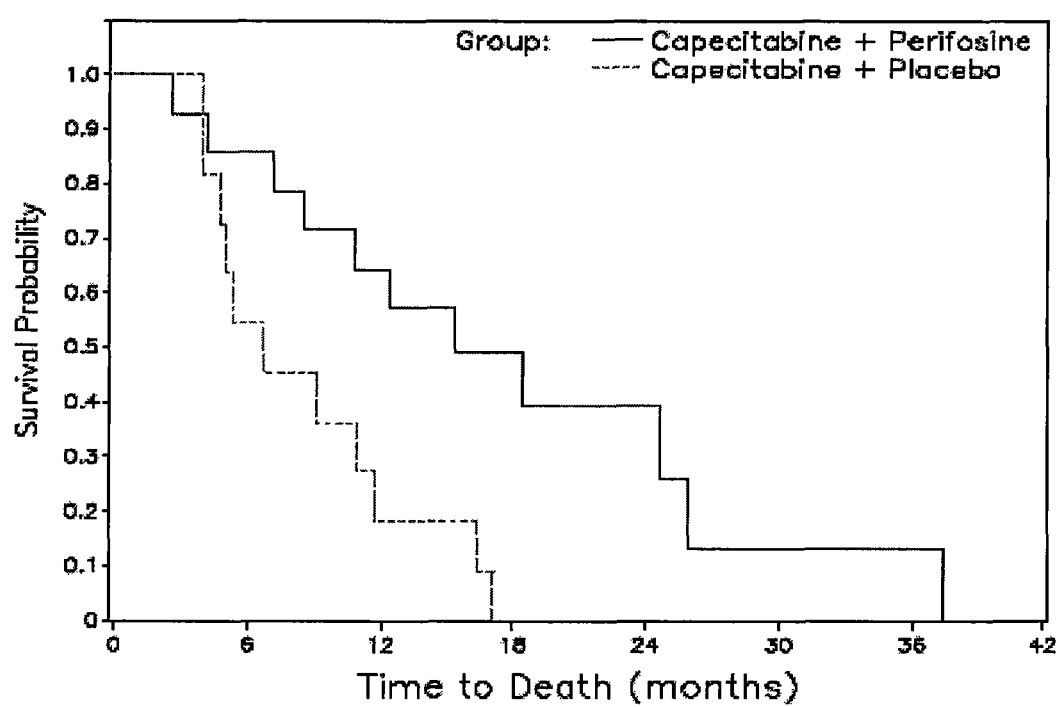
FIG. 4 is a graph showing the survival probability for tested 5-fluorouracil-refractory metastatic colorectal cancer patients, as a function of time, when administered 1650 mg/m$^2$ per day capecitabine (days 1-14 every 21 days) with 50 mg per day perifosine or 1650 mg/m$^2$ per day capecitabine (days 1-14 every 21 days) with a placebo.

FIGS. 3 and 4 show that perifosine had similarly beneficial effects in 5-fluorouracil-refractory metastatic colorectal cancer patients.

As described in the Examples section that follows, the above-mentioned beneficial effect of perifosine which was observed in subjects receiving capecitabine was surprisingly found not to occur in subjects receiving any of a wide variety of other chemotherapeutic agents (i.e., gemcitabine, paclitaxel, docetaxel, doxorubicin, pemetrexed, irinotecan and pegylated liposomal doxorubicin). The above-mentioned beneficial effect of perifosine is therefore not merely an additive effect of the effects of perifosine and capecitabine, but rather results from a specific synergistic interaction between perifosine and capecitabine. Thus, combining the two drugs results in increase of efficacy of either drug alone. The combinations of perifosine and capecitabine described herein provide synergistic therapeutic benefits in terms of both safety (e.g., by allowing dose reduction) and efficacy (e.g., by increasing the efficacy of a given dose). Accordingly, embodiments of the present disclosure relate to methods and compositions that utilize a synergistic combination of perifosine and capecitabine.

Hence, according to an aspect of some embodiments of the disclosure there is provided a method of treating cancer in a subject in need thereof. The method, according to these embodiments, is effected by administering to the subject a therapeutically effective amount of perifosine and a therapeutically effective amount of capecitabine.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition, and includes, for example, reducing a size of a tumor in a subject, effecting a state of remission in a subject, increasing an expected survival probability, increasing life expectancy, and increasing an expected time to disease progression.

As described in the Examples section that follows, perifosine and capecitabine were surprisingly observed to have a beneficial synergistic effect when administered with one another, and this synergistic effect was not observed between perifosine and chemotherapeutic agents other than capecitabine.

Herein, "administering" and "administration" refer to the application of an active ingredient to the body of a subject.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections. Alternately, one may administer the pharmaceutical composition in a local rather than systemic manner, for example, via injection of the pharmaceutical composition directly into a tissue region of a patient.

Oral administration is an exemplary administration for both perifosine and capecitabine, as described in the Examples section below.

It is to be understood that administration of perifosine and capecitabine need not be via the same route, and need not be performed simultaneously.

As both perifosine and capecitabine can be administered orally, the above method may be effected by orally administering one or both of the perifosine and capecitabine. In some embodiments, administering perifosine is effected once per day. In some embodiments, administering capecitabine is effected once per day. In some embodiments, administering capecitabine is effected twice per day.

As used herein, a "therapeutically effective amount" means an amount of an active ingredient (perifosine or capecitabine) which, in the context of the combined therapy described herein comprising perifosine in combination with capecitabine, is effective to treat a cancer, as defined herein, alleviate or ameliorate symptoms of a cancer, and/or prolong the survival of the subject being treated.

The therapeutically effective amount of perifosine is optionally in a range of from 10 mg per day to 200 mg per day, optionally in a range of from 10 mg per day to 100 mg per day, optionally in a range of from 20 mg per day to 80 mg per day, and optionally in a range of from 40 mg per day to 60 mg per day. According to exemplary embodiments, the therapeutically effective amount of perifosine is 50 mg per day.

The therapeutically effective amounts of perifosine described herein refer to therapeutically effective amounts for administration to adult subjects. Optionally, amounts of perifosine to be administered a child are adjusted, for example, according to body weight of the child.

According to some embodiments, the therapeutically effective amounts of perifosine described herein are absolute, and do not depend on the body size (e.g., body weight, body surface area) of the subject, with the optional exception of subjects with a body weight far from the adult average (e.g., children).

According to alternative embodiments, the therapeutically effective amounts of perifosine described herein are considered suitable for a subject of average body size (e.g., a body weight of 70 kg, a body surface area of 1.73 m$^2$), and the amount to be administered is adjusted according to the body size (e.g., body weight, body surface area) of the subject receiving perifosine. For example, a dose of 50 mg per day recited herein is optionally understood to refer to a dose of 50 mg per day per 1.73 m$^2$ body surface area. Thus, for example, for a subject having a body surface area of 1.9 m$^2$ (i.e., 110% of 1.73 m$^2$), a dose of 55 mg (i.e., 110% of 50 mg) per day for that subject would be indicated.

In some embodiments, a therapeutically effective amount of perifosine is determined according to available unit dosage forms. For example, a suitable amount of perifosine may be determined as described herein, and then adjusted to the nearest amount which may be conveniently administered using available unit dosage forms. Optionally, perifosine is administered once every 2 days or 3 days, so as to optimize the amount of perifosine administered per day (i.e., the average amount per day).

The daily doses of perifosine which may be administered conveniently using unit dosage forms are amounts divisible by half the unit dosage form. Thus, for example, perifosine is currently available in tablets comprising 50 mg perifosine, such that exemplary convenient therapeutically effective amounts are amounts divisible by 25 mg per day.

Hence, in some embodiments, the therapeutically effective amount of perifosine administered per day is divisible by 25 mg. Thus, for example, administration of 100 mg per day may be effected by administering two 50 mg tablets per day; administration of 75 mg per day may be effected by administering three 50 mg tablets every two days (e.g., administration of three tablets once every two days, or administration of one tablet and two tablets on alternating days, or administering 1 and a half tablet every day); administration of 50 mg per day may be effected by administering one 50 mg tablet per day; and administration of 25 mg per day may be effected by administering one 50 mg tablet every two days or half a tablet every day.

According to some embodiments, a physician may determine that 70 mg perifosine per day is a suitable dose of perifosine for a particular subject (e.g., based on a body surface area of the subject). The physician could then determine that the therapeutically effective amount of perifosine will be 75 mg per day, which may be administered as described hereinabove using 50 mg unit dosage forms.

Dosages divisible by an amount other than 25 mg per day are also contemplated, and will depend on the available unit dosage forms.

According to some embodiments of the present disclosure, the therapeutically effective amount of capecitabine is in a range of from 1500 mg/m$^2$ per day to 1800 mg/m$^2$ per day, optionally in a range of from 1550 mg/m$^2$ per day to 1750 mg/m$^2$ per day, and optionally in a range of from 1600 mg/m$^2$ per day to 1700 mg/m$^2$ per day. According to exemplary embodiments, the therapeutically effective amount of capecitabine is 1650 mg/m$^2$ per day.

The above doses represent a very considerable (~35%) decrease from the recommended dose of 2500 mg/m$^2$ capecitabine per day, and therefore can significantly reduce the severity of side effects associated with capecitabine. In addition, it would be expected that the anti-cancer effect of the above doses would be significantly lower than the anti-cancer effect of 2500 mg/m$^2$ capecitabine per day. However, as described in the Examples below, the present inventors have demonstrated in Phase II clinical trials that that the above-mentioned dosages of capecitabine are effective when co-administered with perifosine.

According to some embodiments, the therapeutically effective amounts of capecitabine described herein are calculated for the subject by determining the body surface area of the subject (e.g., according to a weight and height of the subject). One of skill in the art will be aware of various methods and formulas for calculating a body surface area (e.g., Dubois & Dubois formula, Mosteller formula, Haycock formula, Gehan & George formula, Boyd formula, Fujimoto formula, Takahira formula).

According to alternative embodiments, the therapeutically effective amounts of capecitabine described herein are calculated for the subject using a suitable estimate of the body surface area based on general features (e.g., age, sex) of the patient (e.g., 1.73 m$^2$ for an adult, 1.9 m$^2$ for a man, 1.6 m$^2$ for a woman, 1.14 m$^2$ for a 10-year old child, and the like).

For example, using the above value of 1.73 m$^2$ for an adult, the abovementioned therapeutically effective amount of from 1500 mg/m$^2$ to 1800 mg/m$^2$ capecitabine per day corresponds to a therapeutically effective amount of from 2595 mg to 3114 mg capecitabine per day. Absolute values (i.e., in mg units rather than mg/m$^2$ units) obtained by such calculations (e.g., using the value of 1.73 m$^2$ or an alternative value) can be used, for example, to calculate therapeutically effective amounts for unit dosage forms of capecitabine.

In some embodiments, a therapeutically effective amount of capecitabine is determined according to available unit dosage forms (e.g., as discussed hereinabove for perifosine). For example, a suitable amount of capecitabine may be determined as described herein, and then adjusted to the nearest amount which may be conveniently administered using available unit dosage forms.

The daily doses of capecitabine which may be administered most conveniently using unit dosage forms are amounts which may be obtained from available unit dosage forms. Thus, for example, capecitabine is currently available in tablets comprising 500 mg or 150 mg capecitabine. Many doses divisible by 50 mg may be administered by using a suitable number of 500 mg and/or 150 mg tablets. In some embodiments, a daily dose is selected so as to be divisible by 500 mg, so that the daily dose may be given entirely as 500 mg tablets.

According to some embodiments, a physician may calculate that 3170 mg capecitabine per day is a suitable dose of capecitabine for a particular subject (e.g., based on a body surface area of the subject) according to embodiments of the disclosure. The physician could then determine that the therapeutically effective amount of capecitabine will be 3150 mg per day, which may be administered, for example, using six tablets per day of 500 mg capecitabine and one tablet per day of 150 mg capecitabine. Alternatively, the therapeutically effective dose may be determined as 3000 mg per day, so as to allow administration using only tablets of 500 mg capecitabine (i.e., six such tablets).

As used herein, the phrase "per day" describes an amount administered on those days when an agent is administered. The phrase "per day" does not indicate that an amount is administered every day.

Thus, for example, capecitabine may optionally be administered on only some days (e.g., days 1-14 of a 21 day cycle), and the therapeutically amounts of capecitabine described herein refers to an amount administered on such days (e.g., days 1-14) and not to an average amount administered during a period of time in which capecitabine is not administered every day (e.g., an average over 21 days).

In some embodiments, the method according to this aspect of embodiments of the disclosure is effected by co-administering perifosine and capecitabine as described herein in one or more treatment cycles, each cycle being a 21-day cycle. Some or all of the cycles may optionally be followed by evaluation of the health of the patient (e.g., with respect to disease progression and/or adverse side effects) before the next cycle, if required, is effected.

In some embodiments, in each cycle, capecitabine and perifosine are co-administered as described herein on days 1-14, whereby on days 15-21 only perifosine is administered.

In some embodiments, perifosine is administered once a day and capecitabine is administered twice a day.

In some embodiments, a subject treated according to the above-described regimen is administered one time a day with the daily dose of perifosine and part of the daily dose of capecitabine, and one time a day with the rest of the daily dose of capecitabine. In some embodiments, half of the daily dose of capecitabine is administered with perifosine and the other half is administered alone.

In some embodiments, a subject treated according to the above-described regimen is administered one time a day with part (e.g., half) of the daily dose of perifosine and part (e.g., half) of the daily dose of capecitabine, and one time a day with the rest of the daily dose of perifosine and the rest of the daily dose of capecitabine.

In some embodiments, the daily dose of capecitabine is divided into three administrations per day (e.g., each of ⅓ the daily dose). Optionally, perifosine is administered once per day (e.g., along with one of the administrations of capecitabine). Alternatively, the daily dose of perifosine is also divided into three administrations per day (e.g., each of ⅓ the daily dose), which are given along with the three daily administrations of capecitabine.

In order to reduce inconvenience and/or confusion for the subject, it is preferable to minimize the number of daily administrations of medication. To this effect, perifosine can be administered concurrently with an administration of capecitabine, such that perifosine and capecitabine are given in a single administration of medication. In addition, capecitabine can be administered in as few administrations per day as possible without creating undesirable phenomena such as reduced therapeutic efficiency and/or significant increase in severity of side effects. Two administrations per day of capecitabine is a suitable regimen, given the aforementioned considerations. Perifosine may be administered once per day without resulting in reduced therapeutic efficiency or a significant increase in severity of side effects. However, if perifosine is administered concurrently with capecitabine, there is no particularly strong benefit in having fewer administrations per day of perifosine than of capecitabine, as the total number of administrations of medication per day is not affected.

Administrations may be performed in the morning (e.g., along with breakfast) and in the evening (e.g., along with dinner or at bedtime). For example, capecitabine may be administered in both mornings and evenings, with perifosine being administered only in the morning. Alternatively, the perifosine may be administered only in the evening.

Optionally, perifosine and/or capecitabine is administered along with food, i.e., during or soon (e.g., up to 1 hour) after a meal (e.g., breakfast, dinner).

As discussed hereinabove and exemplified in the Examples section below, perifosine exhibits a beneficial effect when combined with administration of approximately 1650 mg/m$^2$ capecitabine per day. 1650 mg/m$^2$ capecitabine per day is considerably lower than the recommended dose for capecitabine, which helps to overcome the considerable adverse side effects expected when combining two anti-cancer agents (i.e., perifosine and capecitabine), as the side effects of capecitabine are considerably reduced by the low dose. However, the low dose of capecitabine is unlikely to provide a full therapeutic benefit of capecitabine treatment.

As described in the Examples section below, the combination of perifosine and capecitabine was found to be relatively safe and well tolerated even when a dose of 2000 mg/m$^2$ capecitabine per day is used, despite the fact that such doses of capecitabine exhibit significant levels of adverse side effects when taken alone.

Hence, according to an aspect of some embodiments of the present disclosure, there is provided a method of treating cancer in a subject in need thereof, the method comprising administering to the subject a therapeutically effective amount of perifosine and a therapeutically effective amount of capecitabine, wherein the therapeutically effective amount of perifosine ranges from 10 mg per day to 200 mg per day and the therapeutically effective amount of capecitabine ranges from 1850 mg/m$^2$ per day to 2150 mg/m$^2$ per day, optionally in a range of from 1900 mg/m$^2$ per day to 2100 mg/m$^2$ per day, and optionally in a range of from 1950 mg/m$^2$ per day to 2050 mg/m$^2$ per day. According to exemplary embodiments, the therapeutically effective amount of capecitabine is 2000 mg/m$^2$ per day.

Without being bound by any particular theory, it is believed that the abovementioned dosages of capecitabine in a range of from 1850 mg/m$^2$ per day to 2150 mg/m$^2$ per day result in a dose of capecitabine for co-treatment with perifosine. For example, it is believed that such dosages of capecitabine, when co-administered with perifosine, combine the therapeutic effectiveness of higher amounts of capecitabine (such as the standard dosage of 2500 mg/m$^2$ per day) with the relatively good tolerance observed with lower amounts of capecitabine. Thus, as described in the Examples section that follows, the present inventors have found that 2000 mg/m$^2$ capecitabine with co-administration of perifosine is well tolerated. The doses of capecitabine and perifosine provide a synergistic combination for treating a cancer.

Suitable routes of administration of perifosine and capecitabine are described hereinabove. Oral administration is an exemplary administration for both perifosine and capecitabine, as described in the Examples section that follows.

Therapeutically effective amounts of perifosine according to optional embodiments are described hereinabove, along with optional methods for determining a suitable therapeutically effective amount for a subject (e.g., based on a body surface area of a subject and/or available unit dosage forms of perifosine).

As both perifosine and capecitabine can be administered orally, the above method may be effected by orally administering one or both of the perifosine and capecitabine. In some embodiments, administering perifosine is effected once per day. In some embodiments, administering capecitabine is effected once per day. In some embodiments, administering capecitabine is effected twice per day.

The above doses represent a considerable (nearly 20%) decrease from the recommended dose of 2500 mg/m$^2$ capecitabine per day, and therefore can significantly reduce the severity of side effects associated with capecitabine. In addition, it would be expected that the anti-cancer effect of the above doses would be significantly lower than the anti-cancer effect of 2500 mg/m$^2$ capecitabine per day. However, due to the synergy between perifosine and capecitabine discussed herein, there is little or no reduction in therapeutic effect of the abovementioned regimen comprising a reduced dose of capecitabine along with perifosine, as compared to administration 2500 mg/m$^2$ capecitabine per day without perifosine.

According to some embodiments, the therapeutically effective amounts of capecitabine described herein are calculated for the subject by determining the body surface area of the subject (e.g., according to a weight and height of the subject), as described hereinabove.

According to alternative embodiments, the therapeutically effective amounts of capecitabine described herein are calculated for the subject using a suitable estimate of the body surface area based on general features (e.g., age, sex) of the patient, as described hereinabove.

In some embodiments, a therapeutically effective amount of capecitabine is determined according to available unit dosage forms, as discussed hereinabove.

Capecitabine may optionally be administered on only some days (e.g., days 1-14 of a 21 day cycle), and the therapeutically amounts of capecitabine described herein refers to an amount administered on such days (e.g., days 1-14) and not to an average amount administered during a period of time in which capecitabine is not administered every day (e.g., an average over 21 days).

In some embodiments, the method according to this aspect of embodiments of the disclosure is effected by co-administering perifosine and capecitabine as described herein in one or more treatment cycles, each cycle being a 21-day cycle. Some or all of the cycles may optionally be followed by evaluation of the health of the patient (e.g., with respect to disease progression and/or adverse side effects) before the next cycle, if required, is effected.

In some embodiments, in each cycle, capecitabine and perifosine are co-administered as described herein on days 1-14, whereby on days 15-21 only perifosine is administered.

In some embodiments, perifosine is administered once a day and capecitabine is administered twice a day.

In some embodiments, a subject treated according to the above-described regimen is administered one time a day with the daily dose of perifosine and part of the daily dose of capecitabine, and one time a day with the rest of the daily dose of capecitabine. In some embodiments, half of the daily dose of capecitabine is administered with perifosine and the other half is administered alone.

In some embodiments, a subject treated according to the above-described regimen is administered one time a day with part (e.g., half) of the daily dose of perifosine and part (e.g., half) of the daily dose of capecitabine, and one time a day with the rest of the daily dose of perifosine and the rest of the daily dose of capecitabine.

In some embodiments, the daily dose of capecitabine is divided into three administrations per day (e.g., each of ⅓ the daily dose). Optionally, perifosine is administered once per day (e.g., along with one of the administrations of capecitabine). Alternatively, the daily dose of perifosine is also divided into three administrations per day (e.g., each of ⅓ the daily dose), which are given along with the three daily administrations of capecitabine. The number of administrations per day of perifosine and capecitabine according to embodiments of the disclosure may be determined as described hereinabove.

Administrations may be performed in the morning (e.g., along with breakfast) and in the evening (e.g., along with dinner or at bedtime), as described hereinabove.

Optionally, perifosine and/or capecitabine is administered along with food, i.e., during or soon (e.g., up to 1 hour) after a meal (e.g., breakfast, dinner).

According to some embodiments, in any of the methods described herein, administering the capecitabine comprises administering twice per day a dosage unit form which comprises a suitable amount (e.g., 1000 mg/m$^2$, 825 mg/m$^2$) of capecitabine, as described herein.

Optionally, dosage unit forms comprise an amount of capecitabine based on an estimated body surface weight, as described hereinabove.

Embodiments of the present disclosure are particularly suitable for treatment of cancers for which capecitabine is recognized (e.g., by the U.S. Food and Drug Administration) as being effective against, although treatment of additional cancer types (including carcinomas, sarcomas, lymphomas, leukemias, and germ cell tumors is also contemplated. Examples include a colorectal cancer and a breast cancer. Optionally, the cancer is metastatic. Colorectal cancer, optionally metastatic, is an exemplary cancer treatable according to embodiments described herein.

As used herein, the term "metastatic" refers to a cancer for which there is known to exist at least one tumor (a "secondary tumor") in an organ other than the organ which is the source of the tumor cells. For example, colorectal cancer has a tendency to spread from the colon or rectum to lymph nodes and then to the liver. The organ which is the source of the tumor cells can be identified using standard methods in the art.

As used herein, the phrase "colorectal cancer" refers to a cancer of the colon, rectum or appendix (that is, at least one of the aforementioned organs is a source of tumor cells).

It is expected that during the life of a patent maturing from this application, capecitabine may be identified as being effective against various additional cancers, and the scope of the phrase "cancers for which capecitabine is recognized as being against" is intended to include all such cancer types a priori.

In addition, embodiments of the present disclosure are suitable for treatment of cancers which exhibit (or are likely to exhibit) at least some resistance to a chemotherapeutic agent, for example a chemotherapeutic agent which has previously been administered to the subject.

Hence, according to some embodiments, the embodiments described herein (e.g., methods, compositions, etc.) are for treating a subject that has received a prior chemotherapy treatment.

According to some embodiments, any of the methods described herein is utilized for treating a subject having cancer (e.g., colorectal cancer), which is characterized by a resistance to a chemotherapeutic agent. Such a subject has received a prior chemotherapy treatment. The resistance can be an acquired resistance to the prior chemotherapeutic agent(s) used. Exemplary such chemotherapeutic agents include, but are not limited to, paclitaxel, an anthracycline, a fluoropyrimidine (e.g., 5-fluorouracil), irinotecan, oxaliplatin, bevacizumab, cetuximab and panitumumab.

Alternatively, the resistance can be an inherent resistance.

As used herein, the term "fluoropyrimidine" refers to a chemotherapeutic agent comprising a pyrimidine ring, wherein the pyrimidine ring is substituted by at least one fluorine atom. Examples of fluoropyrimidines include 5-fluorouracil, floxuridine, tegafur and capecitabine.

According to some embodiments, any of the methods described herein is utilized for treating a subject having cancer (e.g., colorectal cancer), whereby the subject received a prior chemotherapy treatment but has shown intolerance to the chemotherapeutic agent(s) used.

Herein, a subject is considered to be intolerant of a chemotherapy treatment when the treatment was stopped, on the advice of a physician administering the treatment, as a result of adverse side effects caused by the treatment (e.g., toxicity).

Oxaliplatin toxicity is an exemplary form of intolerance to a chemotherapy treatment. Treatment of patients intolerant of oxaliplatin is exemplified in the Examples section below.

In addition, as discussed herein, the synergy between perifosine and capecitabine allows a reduction of the amount of capecitabine to be administered, thereby reducing the side effects caused by capecitabine. Hence, embodiments of the present disclosure are particularly suitable for overcoming intolerance to capecitabine and related chemotherapeutic agents (e.g., fluoropyrimidines).

In view of the beneficial synergy between perifosine and capecitabine described herein, perifosine may be prepared with a specific purpose of being co-administered with capecitabine.

Hence, according to another aspect of embodiments of the present disclosure, there is provided a pharmaceutical composition which comprises a therapeutically effective amount of perifosine with other chemical components such as pharmaceutically acceptable and suitable carriers and excipients, as detailed herein.

According to some embodiments of the disclosure, the pharmaceutical composition is being packaged in a packaging material and identified, in or on the packaging material, for use in combination with a therapeutically effective amount of capecitabine, for the treatment of cancer (e.g., a cancer as described herein), the pharmaceutical composition being formulated for oral administration.

In some embodiments, one or more unit dosage forms are packaged in a packaging material, as described hereinabove, each unit dosage form comprising a therapeutically effective amount of perifosine, as described hereinabove, suitable for 1 day (e.g., from 10 to 200 mg perifosine). Optionally, such a pharmaceutical composition is further identified for administration once per day.

Optionally, the pharmaceutical composition is identified for use in a subject receiving capecitabine twice per day or three times per day, as described herein. The pharmaceutical composition may be administered concurrently with capecitabine (e.g., one of two administrations per day of capecitabine).

The therapeutically effective amount of perifosine is optionally in a range of from 10 mg to 200 mg, optionally in a range of from 10 mg to 100 mg, optionally in a range of from 20 mg to 80 mg, and optionally in a range of from 40 mg to 60 mg. According to exemplary embodiments, the therapeutically effective amount of perifosine is 50 mg.

According to some embodiments of the present disclosure, the therapeutically effective amount of capecitabine for use in combination with the pharmaceutical composition is in a range of from 1500 $mg/m^2$ per day to 1800 $mg/m^2$ per day, optionally in a range of from 1550 $mg/m^2$ per day to 1750 $mg/m^2$ per day, and optionally in a range of from 1600 $mg/m^2$ per day to 1700 $mg/m^2$ per day. According to exemplary embodiments, the therapeutically effective amount of capecitabine is 1650 $mg/m^2$ per day.

According to alternative embodiments, the therapeutically effective amount of capecitabine for use in combination with the pharmaceutical composition is in a range of from 1850 $mg/m^2$ per day to 2150 $mg/m^2$ per day, optionally in a range of from 1900 $mg/m^2$ per day to 2100 $mg/m^2$ per day, and optionally in a range of from 1950 $mg/m^2$ per day to 2050 $mg/m^2$ per day. According to exemplary embodiments, the therapeutically effective amount of capecitabine is 2000 $mg/m^2$ per day.

According to some embodiments, the therapeutically effective amount of capecitabine for use in combination with the pharmaceutical composition is calculated for the subject by determining the body surface area of the subject (e.g., according to a weight and height of the subject), as described herein.

According to alternative embodiments, the therapeutically effective amounts of capecitabine described herein are calculated for the subject using a suitable estimate of the body surface area based on general features (e.g., age, sex) of the patient, as described herein.

In some embodiments, a therapeutically effective amount of capecitabine is determined according to available unit dosage forms, as described hereinabove.

The pharmaceutical composition may optionally be identified for use in combination with capecitabine on only some days (e.g., days 1-14 of a 21 day cycle). In such embodiments, the therapeutically amounts of capecitabine described herein refers to an amount administered on such days (e.g., days 1-14), and not to an average amount administered during a period of time in which capecitabine is not administered every day (e.g., an average over 21 days).

In some embodiments, the pharmaceutical composition is identified for use in combination with capecitabine in one or more treatment cycles, each cycle being a 21-day cycle. Some or all of the cycles may optionally be followed by evaluation of the health of the patient (e.g., with respect to disease progression and/or adverse side effects) before the next cycle, if required, is effected.

In some embodiments, in each cycle, capecitabine and the pharmaceutical composition comprising perifosine are co-administered as described herein on days 1-14, whereby on days 15-21 only the pharmaceutical composition is administered.

The pharmaceutical composition comprising perifosine may be identified for administration in the morning (e.g., along with breakfast) and/or in the evening (e.g., along with dinner or at bedtime), as described hereinabove.

Optionally, the pharmaceutical composition is administered along with food, i.e., during or soon (e.g., up to 1 hour) after a meal (e.g., breakfast, dinner).

In other embodiments, one or more unit dosage forms are packaged in a packaging material, and each unit dosage form comprising one half of a therapeutically effective amount of perifosine, as described hereinabove, suitable for 1 day (e.g., from 5 to 100 mg perifosine). Optionally, such a pharmaceutical composition is further identified for administration twice per day.

In some embodiments, the pharmaceutical composition unit dosage form is identified for use by administering once per day two unit dosage forms concurrently for a normal adult, by administering one unit dosage per day for a subject with a small body size (e.g., a child).

Optionally, the pharmaceutical composition is identified for use in a subject receiving capecitabine twice per day or three times per day, as described herein. The pharmaceutical composition may be administered concurrently with capecitabine (e.g., the pharmaceutical composition is administered twice per day concurrently with two daily administrations of capecitabine).

The therapeutically effective amount of perifosine is optionally in a range of from 5 mg to 100 mg, optionally in a range of from 5 mg to 50 mg, optionally in a range of from 10 mg to 40 mg, and optionally in a range of from 20 mg to 30 mg. According to exemplary embodiments, the therapeutically effective amount of perifosine is 25 mg.

According to some embodiments of the present disclosure, the therapeutically effective amount of capecitabine for use in combination with the pharmaceutical composition is in a range of from 1500 mg/m$^2$ per day to 1800 mg/m$^2$ per day, optionally in a range of from 1550 mg/m$^2$ per day to 1750 mg/m$^2$ per day, and optionally in a range of from 1600 mg/m$^2$ per day to 1700 mg/m$^2$ per day. According to exemplary embodiments, the therapeutically effective amount of capecitabine is 1650 mg/m$^2$ per day.

According to alternative embodiments, the therapeutically effective amount of capecitabine for use in combination with the pharmaceutical composition is in a range of from 1850 mg/m$^2$ per day to 2150 mg/m$^2$ per day, optionally in a range of from 1900 mg/m$^2$ per day to 2100 mg/m$^2$ per day, and optionally in a range of from 1950 mg/m$^2$ per day to 2050 mg/m$^2$ per day. According to exemplary embodiments, the therapeutically effective amount of capecitabine is 2000 mg/m$^2$ per day.

According to some embodiments, the therapeutically effective amount of capecitabine for use in combination with the pharmaceutical composition is calculated for the subject by determining the body surface area of the subject (e.g., according to a weight and height of the subject), as described herein.

According to alternative embodiments, the therapeutically effective amounts of capecitabine described herein are calculated for the subject using a suitable estimate of the body surface area based on general features (e.g., age, sex) of the patient, as described herein.

In some embodiments, a therapeutically effective amount of capecitabine is determined according to available unit dosage forms, as described hereinabove.

The pharmaceutical composition may optionally be identified for use in combination with capecitabine on only some days (e.g., days 1-14 of a 21 day cycle). In such embodiments, the therapeutically amounts of capecitabine described herein refers to an amount administered on such days (e.g., days 1-14), and not to an average amount administered during a period of time in which capecitabine is not administered every day (e.g., an average over 21 days).

In some embodiments, the pharmaceutical composition is identified for use in combination with capecitabine in one or more treatment cycles, each cycle being a 21-day cycle. Some or all of the cycles may optionally be followed by evaluation of the health of the patient (e.g., with respect to disease progression and/or adverse side effects) before the next cycle, if required, is effected.

In some embodiments, in each cycle, capecitabine and the pharmaceutical composition comprising perifosine are co-administered as described herein on days 1-14, whereby on days 15-21 only the pharmaceutical composition is administered.

The pharmaceutical composition comprising perifosine may be identified for administration once in the morning (e.g., along with breakfast) and once in the evening (e.g., along with dinner or at bedtime), as described hereinabove.

Optionally, the pharmaceutical composition is administered along with food, i.e., during or soon (e.g., up to 1 hour) after a meal (e.g., breakfast, dinner).

The pharmaceutical composition can be identified in print in the packaging material (e.g., within an insert) or on the packaging material, for use in the treatment of the conditions (e.g., colorectal cancer) indicated herein.

The pharmaceutical composition may be identified by one or more instruction sheets, which may be packaged within the packaging material, indicating the intended use, the recommended route of administration, dosage and regimen of the composition. The instruction sheet(s) optionally indicates whether the pharmaceutical composition is to be taken in the morning or evening, along with capecitabine, before meals, during meals or after meals, and so forth, as described herein.

As used herein, a "pharmaceutical composition" refers to a preparation of at least one active ingredient (e.g., perifosine), or physiologically acceptable salts or prodrugs thereof, with other chemical components, including, but not limited to, physiologically suitable carriers, excipients, lubricants, buffering agents, antibacterial agents, bulking agents (e.g. mannitol), antioxidants (e.g., ascorbic acid or sodium bisulfite), and the like. The purpose of the pharmaceutical composition is to facilitate administration of he at least one active ingredient to a subject.

The term "unit dosage form", as used herein, describes physically discrete units, each unit containing a predetermined quantity of an active ingredient (e.g., perifosine) calculated to produce the desired therapeutic effect, in association with at least one pharmaceutically acceptable carrier, diluent, excipient, or combination thereof.

Herein, the phrases "physiologically acceptable carrier" and "pharmaceutically acceptable carrier", which are used interchangeably, describe a carrier or a diluent that does not cause significant irritation to the subject and does not abrogate the biological activity and properties of the active ingredient(s) in a pharmaceutical composition.

As used herein, the term "carrier" refers to a diluent, adjuvant, excipient, or vehicle with which the therapeutic is administered.

Herein the term "excipient" refers to an inert substance added to a pharmaceutical composition to further facilitate administration of an active ingredient.

Techniques for formulation and administration of drugs may be found in "Remington's Pharmaceutical Sciences" Mack Publishing Co., Easton, Pa., latest edition, which is incorporated herein by reference.

Pharmaceutical compositions of embodiments of the present disclosure may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with embodiments of the present disclosure thus may be formulated in conventional manner using one or more pharmaceutically acceptable carriers comprising excipients and auxiliaries, which facilitate processing of the active ingredient(s) (e.g., perifosine, capecitabine) into preparations which, can be used pharmaceutically. Proper formulation is dependent upon the route of administration chosen.

For injection, the active ingredient(s) of embodiments of the disclosure may be formulated in aqueous solutions, for example in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

For oral administration, the active ingredient(s) can be formulated readily by combining the active ingredient(s) described herein with pharmaceutically acceptable carriers well known in the art. Such carriers enable the active ingredient(s) to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient(s).

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredient(s) described herein may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the active ingredient(s) for use according to embodiments of the present disclosure are conveniently delivered in the form of an aerosol spray presentation (which typically includes powdered, liquefied and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the active ingredient(s) and a suitable powder base such as, but not limited to, lactose or starch.

The active ingredient(s) described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active ingredient(s). Additionally, suspensions of the active ingredient(s) may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the active ingredient(s) to allow for the preparation of highly concentrated solutions.

Alternatively, the active ingredient(s) may be in powder form for constitution with a suitable vehicle, e.g., sterile, pyrogen-free water, before use.

The active ingredient(s) of embodiments of the present disclosure may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

According to some embodiments, the pharmaceutical compositions for use in accordance with embodiments of the present disclosure are formulated for oral administration as described herein.

Perifosine and capecitabine may be provided together in a kit which comprises discrete unit dosage forms of perifosine and unit dosage forms of capecitabine, packaged together in a packaging material. In some embodiments, the kit includes identification of its intended use, namely treating cancer by co-administering perifosine and capecitabine, as described herein. In some embodiments, the kit includes instructions for identifying each of the perifosine and capecitabine, and for instructing when to take a unit dosage form, which unit dosage forms to take, and how many unit dosage forms to take, in accordance with a regimen as described herein. The instructions and identification of the intended use can be provided in and/or on the kit's packaging material, within a package insert, identifying each of the perifosine and capecitabine, and instructing when to take a unit dosage form, which unit dosage forms to take, and how many unit dosage forms to take, in accordance with a regimen as described herein.

Alternatively, perifosine and capecitabine can be formulated together in a pharmaceutical composition unit dosage form.

Hence, according to another aspect of embodiments of the disclosure there is provided a pharmaceutical composition unit dosage form comprising perifosine and capecitabine.

Optionally, each unit dosage form comprising a therapeutically effective amount of perifosine, as described hereinabove, suitable for 1 day (e.g., from 10 to 200 mg perifosine, from 40 to 60 mg perifosine, 50 mg perifosine). Optionally, such a pharmaceutical composition is further identified for administration once per day.

Alternatively, each unit dosage form comprises one half of a therapeutically effective amount of perifosine, as described hereinabove, suitable for 1 day (e.g., from 5 to 100 mg perifosine, from 20 to 30 mg perifosine, 25 mg perifosine). Optionally, such a pharmaceutical composition is further identified for administration twice per day.

According to some embodiments, the unit dosage form further comprises from 2500 to 3200 mg capecitabine, optionally from 2600 to 3100 mg capecitabine, and optionally from 2700 to 3000 mg capecitabine.

According to some embodiments, the unit dosage form further comprises from 3100 to 3800 mg capecitabine, optionally from 3200 to 3700 mg capecitabine, and optionally from 3300 to 3600 mg capecitabine.

According to some embodiments, the unit dosage form further comprises from 1250 to 1600 mg capecitabine, optionally from 1300 to 1550 mg capecitabine, and optionally from 1350 to 1500 mg capecitabine.

According to some embodiments, the unit dosage form further comprises from 1550 to 1900 mg capecitabine, optionally from 1600 to 1850 mg capecitabine, and optionally from 1650 to 1800 mg capecitabine.

In some embodiments, the unit dosage form comprises a therapeutically effective amount of perifosine suitable for 1 day (e.g., as described herein) and half of a therapeutically effective amount of capecitabine suitable for 1 day (e.g., from 1250 to 1600 mg capecitabine, from 1550 to 1900 mg capecitabine). Therapeutically effective amounts of capecitabine suitable for 1 day may optionally be calculated using any suitable daily dose described herein (in mg/m$^2$) and an estimate of body surface area for a normal adult human (e.g., 1.6-1.9 m$^2$, about 1.73 m$^2$).

The unit dosage form is identified for use with a therapeutically effective amount of capecitabine (e.g., a unit dosage form which comprises the capecitabine). Optionally, the therapeutically effective amount is half of a therapeutically effective amount of capecitabine suitable for 1 day (e.g., from 1250 to 1600 mg capecitabine, from 1550 to 1900 mg capecitabine), such that the unit dosage form comprising perifosine and capecitabine, in combination with the additional therapeutically effective amount of capecitabine, provide a therapeutically effective amount of capecitabine suitable for 1 day, as described herein.

The unit dosage form is optionally identified for use by administration of the unit dosage form comprising perifosine and capecitabine once per day in combination with administration of the additional therapeutically effective amount of capecitabine (e.g., unit dosage form of capecitabine) once per day, wherein the administration of the unit dosage form comprising perifosine and capecitabine and administration of the additional capecitabine are at least 8 hours apart, optionally at least 9 hours apart, optionally at least 10 hours apart, and optionally at least 11 hours apart. Optionally, the administrations are about 12 hours apart. Such use results in a single daily administration of perifosine with two administrations per day of capecitabine.

In some embodiments, the unit dosage form comprises a therapeutically effective amount of perifosine suitable for 1 day (e.g., as described herein) and a therapeutically effective amount of capecitabine suitable for 1 day (e.g., from 2500 to 3200 mg capecitabine, from 3100 to 3800 mg capecitabine). Therapeutically effective amounts of capecitabine suitable for 1 day may optionally be calculated as described herein.

The unit dosage form may optionally comprise an immediate release formulation, a delayed release formulation, or an extended release (slow release) formulation.

Optionally, the unit dosage form comprises a combination of any of the aforementioned formulations, for example, an immediate release formulation in combination with a delayed release formulation. Each of the perifosine and capecitabine may optionally be divided among one or more of the aforementioned formulation. In addition, the perifosine and capecitabine may be in the same formulation(s) or in different formulations.

In some embodiments, the capecitabine is formulated for delayed release or extended release. Optionally, perifosine is formulated in such a composition for immediate release. Alternatively or additionally, perifosine is formulated in such a composition for delayed release or extended release (e.g., the same formulation as the capecitabine).

A delayed release or extended release composition is particularly suitable for a unit dosage form comprising a therapeutically effective amount of capecitabine suitable for 1 day, as it may be desirable to avoid exposing a subject all at once to such an amount of capecitabine (e.g., to increase tolerance of capecitabine). Delayed release or extended release of capecitabine can therefore have the effect of dividing such a therapeutic amount of capecitabine into at least two separate administrations of capecitabine per day.

The perifosine and capecitabine may optionally be administered in the form of a slow-release preparation, having a reduced rate of release of the active ingredients, in order to further increase patient convenience and compliance and optionally the efficiency of the active agent. The slower the rate of release, the less the blood concentrations fluctuate within a dosing interval. This enables higher doses to be given less frequently (e.g., once per day). Furthermore, slow-release preparations are beneficial in reducing potential side-effects of the active ingredients due to transiently high peak blood concentrations being reached soon after administration.

Slow release preparations typically include slow release biodegradable carriers. Slow release biodegradable carriers are well known in the art. These are materials that may form particles that may capture therein an active compound(s) and slowly degrade/dissolve under a suitable environment (e.g., aqueous, acidic, basic, etc.) and thereby degrade/dissolve in body fluids and release the active compound(s) therein. The particles can be nanoparticles (i.e., in the nanometer range, e.g., in the range of about 1 to about 500 nm in diameter, about 50-200 nm in diameter, or about 100 nm in diameter).

The rate at which a drug is released is generally dependent on the rate at which the dosage form disintegrates or dissolves. Disintegration greatly increases the drug's surface area in contact with GI fluids, thereby promoting drug dissolution and absorption. Disintegrants and other excipients (e.g., diluents, lubricants, surfactants, binders, dispersants) are often added during manufacture to facilitate these processes. Surfactants increase the dissolution rate by increasing the wettability, solubility, and dispersibility of the drug. Disintegration of solid forms may be retarded by excessive pressure applied during the tableting procedure or by special coatings applied to protect the tablet from the digestive processes of the gut. Hydrophobic lubricants (e.g., magnesium stearate) may bind to the active drug and reduce its bioavailability.

Dissolution rate determines the availability of the drug for absorption. When slower than absorption, dissolution becomes the rate-limiting step. Overall absorption can be controlled by manipulating the formulation. For example, reducing the particle size increases the drug's surface area, thus increasing the rate and extent of GI absorption of a drug whose absorption is normally limited by slow dissolution. Dissolution rate is affected by whether the drug is in salt, crystal, or hydrate form.

Oral slow-release forms are often designed to maintain therapeutic drug concentrations for greater than 12 hours. The absorption rate can be controlled by coating drug particles with wax or other water-insoluble material, by embedding the drug in a matrix from which it is released slowly during transit through the GI tract, or by complexing the drug with ion-exchange resins.

Thus, for example, a slow-release formulation in tablet form, may be based on the use of a hydrophilic polymer which swells in contact with gastrointestinal fluids, to form a gel, which creates a barrier that enrobes the tablet. The barrier limits physical exchanges between the inside of the tablet and the surrounding medium. As a consequence, intrusion of water towards the tablet matrix and diffusion of drug are slowed down, allowing a controlled slow release of the drug.

Various types of polymers may be used as a matrix for the slow-release of drugs, such as polyvinyl chloride, polyethylene polyamides, ethylcellulose, silicone, poly (hydroxyethyl methacrylate), other acrylic co-polymers, and polyvinylacetate-polyvinyl chloride copolymers.

Thus, a slow-release formulation for delivery of the perifosine and capecitabine provides for release of capecitabine (and optionally perifosine) over a period that ranges from about 2 hour to about 24 hours, from about 4 hours to about 24 hours and hence, for release over a period of at least 4 hour, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, or at least 24 hours.

The delayed release/extended release pharmaceutical compositions can be obtained by complexing drug with a pharmaceutically acceptable ion-exchange resin and coating such complexes. The formulations are coated with a substance that will act as a barrier to control the diffusion of the drug from its core complex into the gastrointestinal fluids. Optionally, the formulation is coated with a film of a polymer which is insoluble in the acid environment of the stomach, and soluble in the basic environment of lower GI tract in order to obtain a final dosage form that releases less than 10% of the drug dose within the stomach.

In some embodiments, the unit dosage form is formulated so as to exhibit an immediate release of the capecitabine in the unit dosage form. Optionally, the perifosine is also released in an immediate release.

Immediate release of substantially all the capecitabine is suitable for unit dosage forms comprising a fraction (e.g., half) of a therapeutically effective amount of capecitabine suitable for 1 day, as described herein.

In some embodiments, the unit dosage form is formulated so as to exhibit an immediate release of at least a portion of the perifosine in the unit dosage form and at least a portion of the capecitabine in the unit dosage form, and a delayed release (or extended release) of an additional portion of capecitabine and/or perifosine (e.g., the remaining capecitabine and/or perifosine in the unit dosage form).

In some embodiments, substantially all of the perifosine is released in the aforementioned immediate release.

In some embodiments, substantially all of the perifosine is released in the aforementioned delayed release (or extended release).

In some embodiments, a first portion of the capecitabine is released in the aforementioned immediate release, and a second portion of the capecitabine is released in the aforementioned delayed release. Optionally, the first and second portions both comprise about half of the capecitabine in the unit dosage form.

In some embodiments, the first and second portions of capecitabine both comprise from 1250 to 1600 mg capecitabine, optionally from 1300 to 1550 mg capecitabine, and optionally from 1350 to 1500 mg capecitabine.

In some embodiments, the first and second portions of capecitabine both comprise from 1550 to 1900 mg capecitabine, optionally from 1600 to 1850 mg capecitabine, and optionally from 1650 to 1800 mg capecitabine.

In some embodiments, substantially all of the perifosine in the unit dosage form (e.g., from 10 to 200 mg, optionally from 10 mg to 100 mg, optionally from 20 mg to 80 mg, optionally from 40 to 60 mg, and optionally 50 mg perifosine) is released in an immediate release (e.g., along with the abovementioned first portion of capecitabine).

In other embodiments, substantially all of the perifosine in the unit dosage form (e.g., from 10 to 200 mg, optionally from 10 mg to 100 mg, optionally from 20 mg to 80 mg, optionally from 40 to 60 mg, and optionally 50 mg perifosine) is released in a delayed release (e.g., along with the abovementioned second portion of capecitabine).

In other embodiments, a first portion of the perifosine (e.g., from 5 to 100 mg, optionally from 5 mg to 50 mg, optionally from 10 mg to 40 mg, optionally from 20 to 30 mg, and optionally 25 mg perifosine) is released in an immediate release (e.g., along with the abovementioned first portion of capecitabine), and a second portion of the perifosine (e.g., from 5 to 100 mg, optionally from 5 mg to 50 mg, optionally from 10 mg to 40 mg, optionally from 20 to 30 mg, and optionally 25 mg perifosine) is released in a delayed release (e.g., along with the abovementioned second portion of capecitabine).

Optionally, the unit dosage form is in the form of a tablet wherein one component is in a delayed release layer or core, which may be coated with a delayed release coating and optionally an enteric coating. The other component may then be coated over or layered adjacent to the delayed release core or layer (respectively) in an immediate release layer. This immediate release component layer may be coated with an immediate release coating, an enteric coating, or both.

The unit dosage forms described herein may be provided together in a kit which comprises discrete unit dosage forms comprising both perifosine and capecitabine as described herein packaged together in a packaging material.

In some embodiments, for example, wherein the unit dosage form described herein comprises a full daily dose of perifosine and only a portion of a daily dose of capecitabine, the kit further comprises discrete unit dosage forms of capecitabine packaged in the packaging material.

In some embodiments, the kit includes identification of its intended use, namely treating cancer by administering a unit dosage form comprising perifosine and capecitabine, and optionally by further administering capecitabine, as described herein. In some embodiments, the kit includes instructions for identifying the unit dosage form described herein comprising perifosine and capecitabine (and optionally a unit dosage form of capecitabine), and for instructing when to take a unit dosage form, which unit dosage forms to take, and how many unit dosage forms to take, in accordance with a regimen as described herein. The instructions and identification of the intended use can be provided in and/or on the kit's packaging material, within a package insert, identifying the unit dosage form described herein comprising perifosine and capecitabine (and optionally a unit dosage form of capecitabine), and instructing when to take a unit dosage form, which unit dosage forms to take, and how many unit dosage forms to take, in accordance with a regimen as described herein.

Compositions of the present disclosure may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising perifosine and compositions comprising perifosine and capecitabine, as described herein, formulated in a compatible pharmaceutical carrier may also be prepared, placed in an appropriate container, and labeled for treatment of a cancer, as is detailed herein.

As used herein the term "about" refers to ±5%

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the disclosure may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this disclosure may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination or as suitable in any other described embodiment of the disclosure. Certain features described in the context of various embodiments are not to be considered essential features of those embodiments, unless the embodiment is inoperative without those elements.

Various embodiments and aspects of the present disclosure as delineated hereinabove and as claimed in the claims section below find experimental support in the following examples.

EXAMPLES

Reference is now made to the following examples, which together with the above descriptions, illustrate some embodiments of the disclosure in a non limiting fashion.

Example 1

Phase I Portion of a Phase I/II Clinical Study for Evaluating the Safety of Co-Treatment with 50 mg Perifosine and 1650 mg/m$^2$ Capecitabine A phase I/II randomized placebo-controlled study was performed in order to evaluate the effects of perifosine in combination with various cytotoxic agents (i.e., gemcitabine, paclitaxel, docetaxel, doxorubicin, capecitabine, pemetrexed, irinotecan and pegylated liposomal doxorubicin) and to determine if co-administering perifosine and each of these cytotoxic agents results in synergy, and if such synergy overcomes resistance to chemotherapy in cancer cells.

The study was performed on patients having breast cancer, non-small cell lung cancer, colorectal cancer, prostate cancer, ovarian cancer, head and neck cancer or soft tissue sarcoma, who had received at least one prior chemotherapy regimen. An initial cohort of six patients was treated in combination with perifosine in the open label phase I portion of the study to rule out any unexpected or unusually severe toxicities. Patients receiving these agents were allowed to enter the randomized study only if ≦⅔ patients have grade 3 or 4 toxicities related to perifosine. Initially, the phase I clinical study was performed evaluating the safety of co-treatment with 50 mg perifosine daily in combination with various cytotoxic therapies as mentioned above, including the capecitabine arm which specifically included patients with metastatic breast cancer, colorectal cancer, head and neck cancer and ovarian cancer. In respect to the capecitabine+ perifosine combination, 7 patients were enrolled in the phase I portion. During a 21 day cycle, 50 mg perifosine was administered every day, whereas 825 mg/m² capecitabine was administered orally on days 1-14 of the cycle.

Toxicity was graded according to the NCI CTCAE version 3.0, and dose limiting toxicity was defined as any of the following:

Grade 3 non-hematological toxicity; or
any Grade 4 toxicity.

Regardless of disease sites, all patients were required to have a CT scan of the chest, abdomen, and pelvis every 12 weeks. Evaluation of all lesions for progression or response was made at 12-week intervals. Physical examination, performance status, weight, temperature, blood pressure, and pulse were performed at baseline and week 1 of each cycle, except cycle 1, for which week 2 evaluations were also required. Adverse event evaluations were monitored and reported promptly.

In conclusion, the combination of 50 mg perifosine daily in combination with 825 mg/m² capecitabine twice per day for 14 days every 21 days (i.e., 1650 mg/m² capecitabine per day) was found to be safe and well tolerated, in accordance with the above definition. In addition, one of the three (⅓) colorectal cancer patients treated, who previously was refractory to 5-fluorouracil (5-FU) based chemotherapy (FOLFOX and FOLFIRI) and to cetuximab, achieved stable disease for 49 weeks. 5-FU is the drug moiety of, and active metabolite generated by, the capecitabine prodrug.

Example 2

Phase II Portion of a Phase I/II Clinical Study for Evaluating the Efficacy and Safety of Co-Treatment with Perifosine and Single Agent Chemotherapy As outlined above, the randomized placebo-controlled study was performed in order to evaluate the effects of perifosine in combination with various cytotoxic agents (i.e., gemcitabine, paclitaxel, docetaxel, doxorubicin, capecitabine, pemetrexed, irinotecan and pegylated liposomal doxorubicin) and to determine if co-administering perifosine and each of these cytotoxic agents results in synergy, and if such synergy overcomes resistance to chemotherapy in cancer cells.

The study was performed on patients having breast cancer, non-small cell lung cancer, colorectal cancer, prostate cancer, ovarian cancer, head and neck cancer or soft tissue sarcoma, who had received at least one prior chemotherapy regimen. The prior regimen must have been different than the single agent administered in this study. Each patient received a single agent chemotherapy regimen which was judged by a physician as likely to be as beneficial to the patient as any other available therapy.

Patients received either 50 mg perifosine or placebo daily in combination with single-agent chemotherapy.

The single-agent chemotherapy regimens were as follows:

Paclitaxel: 175 mg/m² every 3 weeks or 80 mg/m² on days 1, 8 and 15 every 4 weeks, by intravenous infusion over 1 to 3 hours (used to treat breast, prostate and lung cancers);

Docetaxel: 75 mg/m² every 3 weeks or 35 mg/m² on days 1, 8 and 15 every 4 weeks, by intravenous infusion over 1 hour (used to treat head and neck, lung, ovarian and prostate cancers);

Gemcitabine: 1000 mg/m² on days 1 and 8 every 3 weeks, by infusion over 30 minutes (used to treat sarcoma and lung, ovarian, breast and head and neck cancers);

Doxorubicin: 60 mg/m² every 3 weeks, by infusion over 30 minutes (used to treat sarcoma and prostate, ovarian, and breast cancers);

Pegylated liposomal doxorubicin: 40 mg/m² every 4 weeks, by infusion over 30 minutes (used to treat sarcoma and ovarian and breast cancers);

Capecitabine: 825 mg/m² twice per day (i.e., 1650 mg/m² per day) on days 1-14 every 3 weeks, administered orally (used to treat breast, colorectal, head and neck, prostate, and ovarian cancers);

Pemetrexed: 500 mg/m² every 3 weeks, by intravenous infusion over 10 minutes (used to treat lung and colorectal cancers); and Irinotecan: 100 mg/m² on days 1, 8 and 15 every 4 weeks, by intravenous infusion over 90 minutes (used to treat sarcoma and colorectal and lung cancers).

As mentioned in Example 1 hereinabove with respect to the capecitabine arm, it was also demonstrated that the above doses can be safely given with 50 mg per day perifosine.

The time to progression (TTP) was a primary endpoint for the various treatment groups. Overall survival (OS) rates and overall response rates (ORR) of the patients and the proportion of progression-free patients were secondary endpoints. In addition, the safety of the combined treatments was also evaluated.

Evidence of improved time to progression in any tumor type with any of the evaluated drugs was used to initiate an expanded study of the evaluated drug and tumor type in order to increase the certainty that an effect of perifosine existed.

Progression and response (complete response or partial response) were determined according to RECIST 1.0 criteria.

The Kaplan-Meier method was used to calculate times to progression and overall survival. Median values of the TTP and OS were calculated, as well as the confidence intervals (CI) of the TTP and OS at a 95% confidence level. P-values were calculated for the differences between different treatments.

Safety of treatments was assessed by monitoring adverse events, which were graded according to the NCI CTCAE version 3.0.

Except for capecitabine, none of the tested chemotherapy regimens exhibited a statistically significant improvement in combination with perifosine as compared to capecitabine alone. Based on these initial results, an expanded study was performed to further study the efficacy and safety of co-treatment of metastatic colorectal cancer with capecitabine and perifosine.

The metastatic colorectal cancer patients in the expanded study had previously been treated with a range of prior therapies (median prior therapies was 2) including a FOLFIRI regimen (5-fluorouracil, leucovorin and irinotecan), a FOLFOX regimen (5-fluorouracil, leucovorin and oxaliplatin), bevacizumab, cetuximab and/or panitumumab.

As shown in FIG. 1, the time to progression (TTP) of metastatic colorectal cancer patients receiving perifosine and capecitabine was significantly longer than the TTP of metastatic colorectal cancer patients receiving capecitabine alone. The median TTP was 28 weeks (12-48 weeks CI) for perifosine with capecitabine, and 11 weeks (9-15.9 weeks CI) for capecitabine alone (P=0.0012; hazard ratio=0.284).

Furthermore, as shown in FIG. 2, the overall survival (OS) of metastatic colorectal cancer patients receiving perifosine and capecitabine was significantly longer than the OS of metastatic colorectal cancer patients receiving capecitabine alone. The median OS was 17.7 months (8.5-24.6 months CI) for perifosine with capecitabine, and 10.9 months (5.0-16.9 months CI) for capecitabine alone (P=0.0161; hazard ratio=0.410).

TTP and OS were also evaluated for the subset of metastatic colorectal cancer patients who had previously been found to be refractory to prior 5-fluorouracil (5-FU) based therapy. The efficacy of perifosine with capecitabine in 5-FU refractory patients was of interest because capecitabine alone has previously been found to have limited efficacy in such patients [Lee et al., *Jpn J Clin Oncol* 2004, 34:400-404].

As shown in FIG. 3, the TTP of 5-FU-refractory metastatic colorectal cancer patients receiving perifosine and capecitabine was significantly longer than the TTP of 5-FU-refractory metastatic colorectal cancer patients receiving capecitabine alone. The median TTP was 18 weeks (12-36 weeks CI) for perifosine with capecitabine, and 10 weeks (6.6-11 weeks CI) for capecitabine alone (P=0.0004; hazard ratio=0.186).

Furthermore, as shown in FIG. 4, the OS of 5-FU-refractory metastatic colorectal cancer patients receiving perifosine and capecitabine was significantly longer than the OS of 5-FU-refractory metastatic colorectal cancer patients receiving capecitabine alone. The median OS was 15.1 months (7.3-22.3 months CI) for perifosine with capecitabine, and 6.8 months (4.8-11.7 months CI) for capecitabine alone (P=0.0112; hazard ratio=0.313).

After 12 weeks of treatment, among the 20 evaluable metastatic colorectal cancer patients who received perifosine with capecitabine, 1 exhibited a complete response, 3 exhibited a partial response, and additional 15 (75%) achieved stable disease (progression-free for 3 months or greater). In contrast, among the 15 evaluable metastatic colorectal cancer patients who received capecitabine alone, none exhibited a complete response, 1 exhibited a partial response, and an additional 6 (40%) achieved stable disease (progression-free for 3 months or greater). The difference between the levels of the patients who achieved stable disease, partial or complete response in the two groups was statistically significant (P=0.036).

Among 5-FU refractory metastatic colorectal cancer patients after 12 weeks of the treatment, among the 14 evaluable patients who received perifosine with capecitabine, 1 exhibited a partial response, and an additional 9 (64%) achieved stable disease (progression-free for 3 months or greater). In contrast, among the 11 evaluable metastatic colorectal cancer patients who received capecitabine alone, none exhibited even a partial response, and 3 (27%) achieved stable disease (progression-free for 3 months or greater).

In addition, the perifosine with capecitabine regimen was relatively well tolerated compared to the capecitabine alone regimen. The most common adverse events are shown in Table 1 below (all Grade 3 & 4 adverse events which occurred in at least 10% of any treatment group are shown therein).

A patient population treated with 50 mg perifosine+2× daily 825 mg/m$^2$ capecitabine was compared to a patient population treated with 50 mg perifosine+2× daily 825 mg/m$^2$ capecitabine. In 5-FU refractory patients, the overall survival (OS) of patients treated with placebo+capecitabine was 6.6 months, as compared to an OS of 15.1 in patients treated with perifosine and capecitabine. In all patients, the OS of patients treated with placebo+capecitabine was 10.9 months, as compared to an OS of 17.7 months in patients treated with perifosine and capecitabine. In 5-FU refractory patients, the median time to progression (TTP) for patients treated with placebo+capecitabine was 11 weeks, as compared to a TTP of 18 weeks for patients treated with perifosine+capecitabine. In all evaluable patients, the median time for placebo+capecitabine administration was 11 weeks, as compared to 28 weeks for perifosine+capecitabine.

The highest Grade 3 and 4 adverse events for perifosine+capecitabine vs. placebo+capecitabine were for hand/foot syndrome (30% vs. 0%) and anemia (15% vs. 0%). Mean time to onset of Grade 3 and 4 hand/foot syndrome following treatment with perifosine+capecitabine was 19 weeks, which was greater than the median time-to-progression following treatment with placebo+capecitabine. Patients treated with placebo+capecitabine did not have sufficient time to develop hand and foot syndrome. In addition, no patients in the perifosine+capecitabine group discontinued treatment due to an adverse event whereas 2 patients in the placebo+capecitabine group discontinued for adverse events.

In summary, co-treatment with perifosine significantly increased the efficacy of the capecitabine regimen (1650 mg/m$^2$ per day). The increase in efficacy was particularly significant among 5-FU-refractory patients. 5-FU is the active metabolite generated upon treatment with capecitabine. The improvement of perifosine+capecitabine over placebo+capecitabine could not expected to be the result of capecitabine by itself. These results indicate that perifosine increases the efficacy of capecitabine due to a specific synergy between the two agents, and not due to an additive effect.

Example 3

In clinical studies conducted in a similar patient population with capecitabine as a single agent the median overall survival was very similar to the observed in the capecitabine/placebo arm in the phase II study (see Table 1 below). These studies are compared to the dose used in combination with perifosine. In several studies a 1250 mg/m2 twice daily dose of capecitabine was used. In other studies, a 1000 mg/m2 twice daily dose of capecitabine was used.

TABLE 1

| Therapy | Median OS | Median TTP | Disease State | Study |
|---|---|---|---|---|
| 50 mg perifosine + 2x daily 825 mg/m2 capecitabine | 15.1 mo. for 5-FU refractory; 17.7 mo. all patients | 18 weeks for 5-FU refractory; 28 weeks all patients | | |
| Placebo + 2x daily 825 mg/m2 capecitabine | 6.6 mo. for 5-FU refractory; 10.9 mo. all patients | 10 weeks for 5-FU refractory; 11 weeks all patients | | |
| 7 patients 2x daily 1250 mg/m2 Capecitabine/ After toxicity, dose diluted to 1000 mg/m2 | 5.2 mos. | 4 mos. | Advancing colorectal cancer (ACRC) | Anticancer Res. 26: 1669-1672 (2006). |
| 2x daily 1000-1250 mg/m2 capecitabine (total daily dose 2000-2500 mg/m2 | 6.1 mos. | 2.8 mos. | ACRC | Acta Oncologica, 2005; 44: 236-239. |

TABLE 1-continued

| Therapy | Median OS | Median TTP | Disease State | Study |
|---|---|---|---|---|
| 2x daily 1250 mg/m2 (total 2500 mg/m2) | 5.3 months | 2.3 months | Metastatic colorectal cancer (MCRC) | Asia-Pac J Clin Oncol. 2011; 82-87. |

The data show that capecitabine could be administered in conventional 2x daily 1250 mg/m² capecitabine resulted in significantly increased toxicity. However, the number of toxic events is significantly reduced by reducing the dose of capecitabine. Second, by reducing the dose of capecitabine in a single drug treatment from 2x daily 1250 mg/m² to 2x daily 825 mg/m², the TTP also reduced significantly. Third, however, the combination of 50 mg perifosine and 2×825 mg/m² capecitabine showed significantly increased OS, as well as a significantly increased TTP over all capecitabine studies.

It is believed that the same synergistic effect will be observed for 50 mg perifosine and 2×1000 mg/m² capecitabine.

Example 4

Phase I Clinical Study for Evaluating the Safety of Co-Treatment with 50 mg of Perifosine and 2000 mg/m² Capecitabine Per Day A Phase I clinical study was performed for evaluating the safety of 50 mg perifosine daily in combination with 1000 mg/m² capecitabine twice per day in patients with refractory advanced colorectal cancer. During a 21 day cycle, perifosine was administered every day, whereas capecitabine was administered orally on days 1-14 of the cycle.

The study was performed on patients having $3^{rd}$ line or higher metastatic colorectal cancer, with no prior exposure to perifosine, and who had received, or were not candidates for, regimens containing 5-fluorouracil, oxaliplatin, irinotecan, bevacizumab, and cetuximab or panitumumab. The patients had at least one measurable lesion, as well as adequate bone marrow, liver and renal function.

Prior to the study, a tolerated regimen was defined as having fewer than 33% of the patients experiencing, after one cycle (21 days) of treatment, a dose limiting toxicity (DLT) attributable to the study drugs when at least 6 patients have been treated with the regimen for one cycle. Toxicity was graded according to the NCI CTCAE version 3.0, and dose limiting toxicity was defined as any of the following:

a) Grade 3 non-hematological toxicity except alopecia, which is not reversible Grade 2 or less within 96 hours; or b) any Grade 4 toxicity.

Hematological profiles and serum chemistry results were obtained prior to initiation of the treatment, on days 1 and 11 of the first cycle, and on day 1 (±3 days) of every cycle thereafter. Physical examination (including vital signs, weight and ECOG performance score) was performed prior to initiation of the treatment, and on day 1 (±3 days) of every cycle thereafter. Adverse event evaluations were monitored and reported promptly.

10 patients were enrolled. The median prior treatment was 3 (range of 2-4). All 10 patients had progressed on prior 5-FU-based therapy (5-FU refractory), with a prior treatment history as follows: FOLFOX (100%); FOLFIRI (100%); bevacizumab (100%); and EGFR antibody (60%). Nine (9) patients were evaluable for safety with no DLT's observed. One (1) patient was inevaluable after stopping study drug after day 2 for a non-related adverse event. Grade 3/4 adverse events greater than 10% included: dyspnea (10%), rash (10%), hyperkalemia (10%) and abdominal pain (10%).

Perifosine plasma concentrations were similar to those previously reported for single agent 50 mg perifosine q.d., suggesting that capecitabine did not influence perifosine disposition. There were no statistically significant differences in PK parameters for capecitabine or its metabolites between Cycle 1 Day 1 (first dose perifosine) and Cycle 1 Day 11 (perifosine for eleven days) suggesting that perifosine had no influence on capecitabine disposition (FINAL DRAFT SUMMARY PHARMACOKINETIC REPORT, Perifosine 141: A Phase I Trial of Perifosine plus Capecitabine for Patients with Advanced Colorectal Cancer). Four patients were stable for 12-46 weeks, 1 patient who was stable at 9 wks, was taken off at week 10 due to a capecitabine related toxicity, further demonstrating encouraging clinical activity in a heavily treated patient population.

The combination of 50 mg perifosine daily in combination with 1000 mg/m² capecitabine twice per day for 14 days every 21 days (i.e., 2000 mg/m² capecitabine per day) was found to be safe and tolerated in patients with refractory advanced colorectal cancer, in accordance with the above definition.

Example 5

Phase I Clinical Study for Evaluating the Safety of Co-Treatment with 50 mg of Perifosine and 2000 mg/m² Capecitabine Per Day A Phase I clinical study was performed for evaluating the safety of 50 mg perifosine daily in combination with 825 mg/m² capecitabine twice per day, compared to a placebo and 825 mg/m² capecitabine twice per day. 18 patients were diagnosed with metastatic breast cancer, 28 patients were diagnosed with metastatic colorectal cancer, and 21 patients were diagnosed with metastatic ovary, head and neck, and prostate cancers.

Figure 5A:
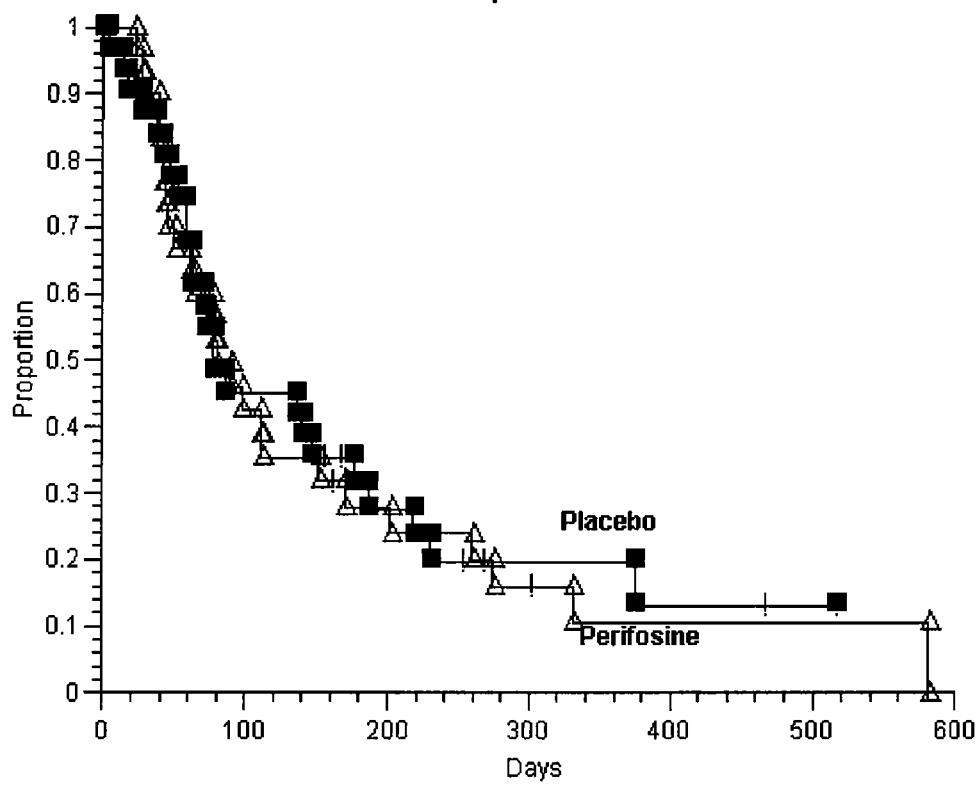
FIGS. 5A and 5B are graphs showing the progression only and all causes of failure, respectively, for patients who were administered 50 mg perifosine, and 825 mg/m² twice daily compared to a placebo and 825 mg/m² twice daily.
Figure 5B:
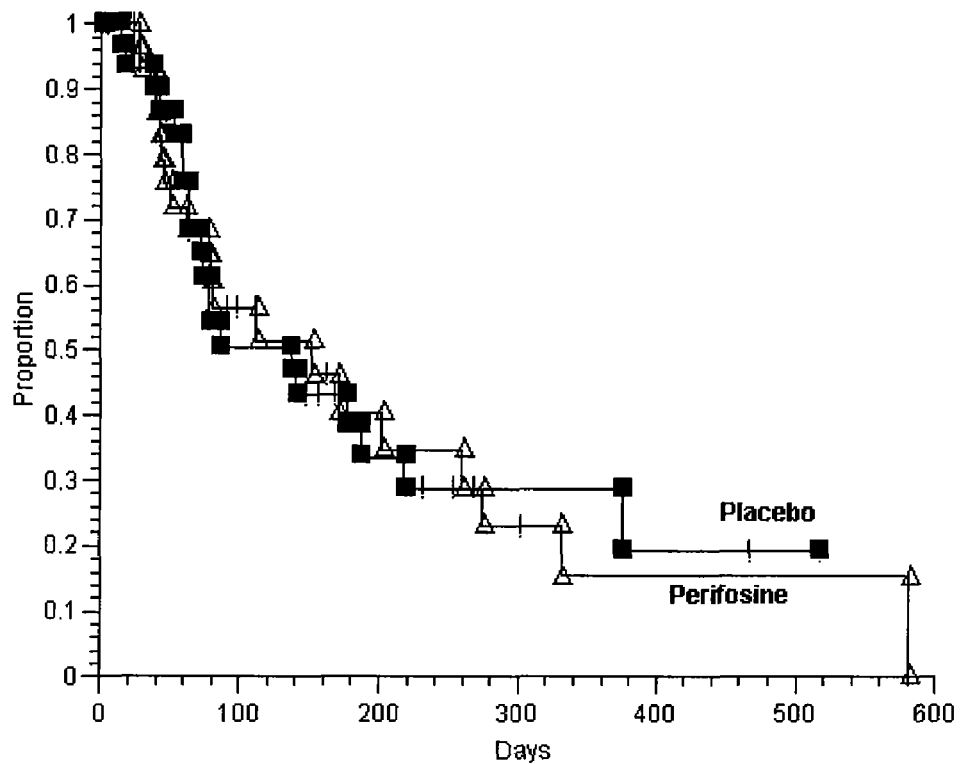

FIGS. 5A and 5B are graphs showing the progression only and all causes of failure, respectively. No change is observed. When compared to the results obtained for perifosine and capecitabine, this implies that in other indications tested in addition to colorectal cancer, there is either no effect or an antagonist effect.

Example 6

Phase III Clinical Study for Evaluating the Efficacy of Co-Treatment with 50 mg Perifosine and 2000 mg/m² Capecitabine Per Day In order to test the hypothesis that 2000 mg/m² per day (e.g., 1000 mg/m² administered twice per day for 14 days every 21 days) of capecitabine for use in combination with 50 mg of perifosine, a randomized, double-blind placebo-controlled Phase III clinical study is performed in order to evaluate a synergistic effect between the perifosine and capecitabine.

The study is performed on patients having adenocarcinoma of the colon or rectum (colorectal) that is recurrent or metastatic. Patients must have failed available therapy for the treatment of advanced colorectal cancer. This is defined as progressive disease during or within 6 months after fluoropyrimidine, irinotecan, oxaliplatin, bevacizumab and for K-ras wild-type (WT) patients, anti-EGFR antibody (cetuximab or panitumumab) containing therapies, with most recent progression by RECIST criteria, or stopping oxaliplatin-based therapy due to toxicity. No prior exposure to capecitabine in the metastatic colorectal cancer setting is allowed, except limited-course radiosensitizing capecitabine (capecitabine given concurrently with radiation therapy for no more than 30 radiation treatment days), which is allowed in the metastatic setting.

Patients are randomly divided (e.g., at a 1:1 ratio) into two treatment arms. Patients take 50 mg perifosine or a placebo tablet daily, and capecitabine at a dose of 1000 mg/m$^2$ twice per day. During a 21 day cycle, perifosine/placebo is administered every day, whereas capecitabine is administered orally on days 1-14 of the cycle. Patients are evaluated for response every 2 cycles (±7 days) for the first 6 cycles, and every 3 cycles (±7 days) thereafter.

In various embodiments, capecitabine may be administered at a dose of 1000 mg/m$^2$ twice per day, 825 mg/m$^2$ twice per day, 750 mg/m$^2$ twice per day, or 500 mg/m$^2$ twice per day.

The objectives of the study are to compare overall survival (OS) of perifosine with capecitabine vs. placebo with capecitabine (e.g., determine whether there is a statistically significant improvement with perifosine at a two-sided 0.05 significance level), and to compare overall response rates (ORR), progression-free survival and TTP.

Radiographic evaluations are performed for progression or response (RECIST 1.1 criteria [Eisenhauer et al., *Eur J Cancer* 2009; 45:228-247]). Progression-free survival, overall response rate and time to progression are based on tumor assessments by a blinded central radiologist.

The study may also include assessing the relationship between perifosine disposition and patient covariates (population pharmacokinetics), exploring the relationship of biomarkers in baseline archived paraffin and optional pre- and on-treatment blood and plasma, peripheral blood mononuclear cell and fresh tumor biopsy samples to efficacy of treatment.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

What is claimed is:

1. A method for treating metastatic colorectal cancer which is characterized by a resistance to a chemotherapeutic agent, comprising administering to a human subject in need thereof 50 mg of perifosine per day and 2000 mg/m$^2$ of capecitabine per day, wherein the perifosine is administered every day and the capecitabine is administered on days 1 to 14 of a 21 day cycle.

2. A method for treating metastatic colorectal cancer which is characterized by a resistance to a fluoropyrimidine, comprising administering to a human subject in need thereof 50 mg of perifosine per day and 2000 mg/m$^2$ of capecitabine per day, wherein the perifosine is administered every day and the capecitabine is administered on days 1 to 14 of a 21 day cycle.

3. A method for treating metastatic colorectal cancer which is characterized by a resistance to 5-fluorouracil, comprising administering to a human subject in need thereof 50 mg of perifosine per day and 2000 mg/m$^2$ of capecitabine per day, wherein the perifosine is administered every day and the capecitabine is administered on days 1 to 14 of a 21 day cycle.

4. A method for treating metastatic colorectal cancer in a human subject characterized as intolerant to a prior chemotherapeutic agent, comprising administering to the human subject 50 mg of perifosine per day and 2000 mg/m$^2$ of capecitabine per day, wherein the perifosine is administered every day and the capecitabine is administered on days 1 to 14 of a 21 day cycle.

5. A method for treating metastatic colorectal cancer in a human subject characterized as intolerant to a 5-fluorouracil, comprising administering to the human subject 50 mg of perifosine per day and 2000 mg/m$^2$ of capecitabine per day, wherein the perifosine is administered every day and the capecitabine is administered on days 1 to 14 of a 21 day cycle.

6. A method for treating metastatic colorectal cancer in a human subject previously treated with an anti-epidermal growth factor receptor antibody, comprising administering to the human subject 50 mg of perifosine per day and 2000 mg/m$^2$ of capecitabine per day, wherein the perifosine is administered every day and the capecitabine is administered on days 1 to 14 of a 21 day cycle.

7. The method of claim 1, wherein the chemotherapeutic agent is paclitaxel, an anthracycline, irinotecan, oxaliplatin, bevacizumab, or an anti-epidermal growth factor receptor antibody.

8. The method of claim 7, wherein the anti-epidermal growth factor receptor antibody is cetuximab or panitumumab.

9. The method of claim 2, wherein the fluoropyrimidine is floxuridine, tegafur or capecitabine.

10. The method of claim 4, wherein the chemotherapeutic agent is paclitaxel, an anthracycline, a fluoropyrimidine, irinotecan, oxaliplatin, bevacizumab, or an anti-epidermal growth factor receptor antibody.

11. The method of claim 10, wherein the fluoropyrimidine is 5-fluorouracil, floxuridine, tegafur or capecitabine.

12. The method of claim 10, wherein the anti-epidermal growth factor receptor antibody is cetuximab or panitumumab.

13. The method of claim 10, wherein the anti-epidermal growth factor receptor antibody is cetuximab or panitumumab.

14. The method of claim 1, wherein the capecitabine is administered twice per day at a dosage of 1000 mg/m$^2$ on days 1 to 14 of a 21 day cycle.

15. The method of claim 2, wherein the capecitabine is administered twice per day at a dosage of 1000 mg/m$^2$ on days 1 to 14 of a 21 day cycle.

16. The method of claim 3, wherein the capecitabine is administered twice per day at a dosage of 1000 mg/m$^2$ on days 1 to 14 of a 21 day cycle.

17. The method of claim 4, wherein the capecitabine is administered twice per day at a dosage of 1000 mg/m$^2$ on days 1 to 14 of a 21 day cycle.

18. The method of claim 5, wherein the capecitabine is administered twice per day at a dosage of 1000 mg/m$^2$ on days 1 to 14 of a 21 day cycle.

19. The method of claim 6, wherein the capecitabine is administered twice per day at a dosage of 1000 mg/m$^2$ on days 1 to 14 of a 21 day cycle.

20. The method of claim 1, wherein the perifosine and capecitabine are orally administered.

21. The method of claim 2, wherein the perifosine and capecitabine are orally administered.

22. The method of claim 3, wherein the perifosine and capecitabine are orally administered.

23. The method of claim 4, wherein the perifosine and capecitabine are orally administered.

24. The method of claim 5, wherein the perifosine and capecitabine are orally administered.

25. The method of claim 6, wherein the perifosine and capecitabine are orally administered.

* * * * *

UNITED STATES PATENT AND TRADEMARK OFFICE
CERTIFICATE OF CORRECTION

PATENT NO. : 8,383,607 B2
APPLICATION NO. : 13/077766
DATED : February 26, 2013
INVENTOR(S) : Enrique Poradosu et al.

It is certified that error appears in the above-identified patent and that said Letters Patent is hereby corrected as shown below:

On the Title page, for item 75,

"Peeter"    should read    "Peter"

On the Title page, for item 60,

"Mar. 31, 2011"    should read    "Mar. 31, 2010"

Signed and Sealed this
Twenty-eighth Day of May, 2013

Teresa Stanek Rea
*Acting Director of the United States Patent and Trademark Office*